(12) United States Patent
Sauve et al.

(10) Patent No.: US 9,322,049 B2
(45) Date of Patent: Apr. 26, 2016

(54) ACTIVATION AND ACTIVATORS OF SIRT6

(75) Inventors: Anthony Sauve, New Rochelle, NY (US); Ping Xu, Brynmawr, PA (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 13/516,198

(22) PCT Filed: Dec. 14, 2010

(86) PCT No.: PCT/US2010/060351
§ 371 (c)(1),
(2), (4) Date: Jun. 14, 2012

(87) PCT Pub. No.: WO2011/081945
PCT Pub. Date: Jul. 7, 2011

(65) Prior Publication Data
US 2013/0029930 A1    Jan. 31, 2013

Related U.S. Application Data

(60) Provisional application No. 61/286,243, filed on Dec. 14, 2009.

(51) Int. Cl.
*A61K 31/70* (2006.01)
*A61K 31/185* (2006.01)
*C12Q 1/48* (2006.01)

(52) U.S. Cl.
CPC ........ *C12Q 1/48* (2013.01); *G01N 2333/91142* (2013.01); *G01N 2500/04* (2013.01)

(58) Field of Classification Search
CPC ................. C12Q 1/48; G01N 2500/04; G01N 2333/91142
USPC .................. 514/43, 52, 576; 562/50; 564/153
See application file for complete search history.

(56) References Cited

U.S. PATENT DOCUMENTS

| | | | |
|---|---|---|---|
| 4,235,871 A | 11/1980 | Papahadjopoulos et al. |
| 4,501,728 A | 2/1985 | Blair et al. |
| 4,837,028 A | 6/1989 | Allen |
| 5,019,369 A | 5/1991 | Presant et al. |

FOREIGN PATENT DOCUMENTS

WO    WO 9307864 A1 * 4/1993

OTHER PUBLICATIONS

Carmichael et al. (Journal of Physical and Chemical Reference Data (1986), 15(1), 1-250)(abstract sent).*
Gagliardi et al. (Cancer Chemotherapy and Pharmacology (1998), 41, 117-124).*
Caswell et al. (Journal of Chemical and Engineering Data (1972), 17(2), 269-71).*
Lockemann et al. (Chemische Berichte (1948), 81, 45-50)(abstract sent).*
CA Registry No. 932231-89-5, entered into the Registry File on Apr. 24, 2007, supplied by Aurora Fine Chemicals.*
Naik et al. (Journal of the Indian Chemical Society (1932), 9, 127-32) (abstract sent).*
Buu-Hoi et al. (Journal of Organic Chemistry (1949), 14, 1023-35).*
Giansante et al. (New Journal of Chemistry (2007), 31(7), 1250-1258).*
Ozeki et al.; JP 45013708 B; May 16, 1970 (abstract sent).*
STN abstract of Buu-Hoi et al. (Journal of Organic Chemistry (1949), 14, 1023-35) (abstract sent).*
STN abstract of Giansante et al. (New Journal of Chemistry (2007), 31(7), 1250-1258) (abstact sent).*
Banker and Chalmers, eds., Pharmaceutics and Pharmacy Practice, J. B. Lippincott Company, Philadelphia, pp. 238-250 (1982).
Conrad, Journal of Pharmaceutical Science, 66, 219-224 (1977).
Lombard et al., J. Intern. Med., 263(2): 128-41(2008).
Michan et al., Biochem J., 404(1): 1-13 (2007).

(Continued)

*Primary Examiner* — Shaojia Anna Jiang
*Assistant Examiner* — Michael C Henry
(74) *Attorney, Agent, or Firm* — Leydig, Voit & Mayer, Ltd.

(57) ABSTRACT

The invention provides a method of increasing a deacetylated activity of SIRT6 by contacting SIRT6 with an agent that binds SIRT6 and reduces the $K_m$ of SIRT6 for a substrate, thereby increasing the deacetylase activity of SIRT6. The invention also provides compounds of the formulas (II) and (III).

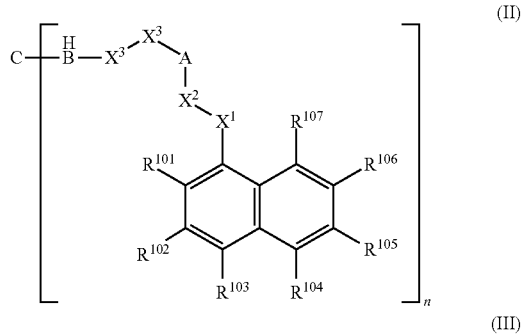

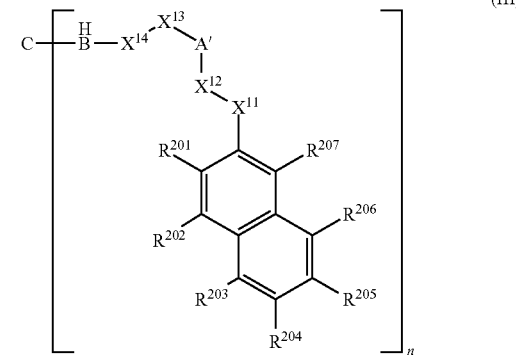

23 Claims, 17 Drawing Sheets

(56) References Cited

OTHER PUBLICATIONS

Michishita et al., Nature, 452(7186): 492-496 (2008).
Michishita et al., Cell Cycle, 8(16): 2664-2666 (2009).
Milne et al., Nature, 450(7170): 712-716 (2007).
Mostoslaysky et al., Cell, 124(2): 315-329 (2006).
Remington's Pharmaceutical Sciences, 18th ed., Mack Publishing Company, Easton, PA, p. 1445 (1990).
Sauve et al., Annu. Rev. Biochem., 75: 435-465 (2006).
Szoka et al., *Ann. Rev. Biophys. Bioeng.*, 9: 467 (1980).
Trapp et al., Chem Med Chem., 2(10): 1419-31 (2007).
Trissel, *ASHP Handbook on Injectable Drugs*, 4th ed., pp. 622-630 (1986).

\* cited by examiner

Deactivated H3    H3

ACTIVATION AND ACTIVATORS OF SIRT6

CROSS-REFERENCE TO RELATED APPLICATIONS

This patent application is the U.S. national phase of International Patent Application No. PCT/US2010/060351, filed Dec. 14, 2010, which claims the benefit of U.S. Provisional Patent Application No. 61/286,243, filed Dec. 14, 2009, each of which is incorporated by reference herein.

STATEMENT REGARDING FEDERALLY SPONSORED RESEARCH AND DEVELOPMENT

This invention was made with Government support under Grant Number R01 DK73466-05 awarded by the NIH. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,033 Byte ASCII (Text) file named "710576_ST25.txt," created on Oct. 9, 2012.

BACKGROUND OF THE INVENTION

The mammalian sirtuin family includes seven nicotinamide adenine dinucleotide (NAD)-dependant deacetylases (SirT1-7), which are implicated in the extension of life span (Michan et al., Biochem J, 404(1): 1-13 (2007); Taylor et al., Chem Med Chem., 2(10): 1419-31 (2007)). SirT1 has been comprehensively studied, and multiple targets such as histone, p53, FOXO, PGC1-α have been identified. By deacetylating and interacting with cellular proteins, SirT1 regulates diverse cellular functions including DNA transcription, stress resistance, apoptosis, glucose homeostasis, insulin secretion and fatty acid metabolism. In contrast, the information about SirT6 is very limited. It is known that SirT6 knock-out mice demonstrated the most striking phenotype among the sirtuins (Lombard et al., J. Intern. Med., 263(2): 128-41 (2008)). SirT6-deficient mice are small and at 2-3 weeks of age develop abnormalities. They have a profound decrease in lymphocyte numbers, low glucose and IGF-1 levels in serum, and low subcutaneous fat (Mostoslaysky et al., Cell, 124(2): 315-29 (2006)). At about 4 weeks, SirT6-deficient mice eventually died. It was demonstrated that SirT6 knock-out mice and cells were very sensitive to DNA damage. SirT6 was shown to be required for the stable association with telomeres of the protein WRN, a DNA metabolic factor that is mutated in the human progeria Werner Syndrome (Michishita et al., Nature, 452(7186): 492-496 (2008)); the DNA DSB repair factor, DNA-dependent protein kinase (DNA-PK) at DSBs (Michishita et al., Cell Cycle, 8(16): 2664-2666 (2009)); and the RELA subunit of NF-κB, a transcription factor involved in apoptosis, cell senescence, inflammation and immunity. These accumulative discoveries reveal the importance of SirT6 in the telemere function, DNA damage repair, genomic stability and stress resistance.

As a nucleus protein, SirT6 was found to be associated with a chromatin-enriched cellular fraction (Mostoslaysky et al., Cell, 124(2): 315-329 (2006)). Another study demonstrated that SirT6 bound to nucleosomes (Michishita et al., Cell Cycle, 8(16), 2664-2666 (2009)) and possessed deacetylation activity on histone H3 lysine 9 (Michishita et al., Nature, 452(7186): 492-496 (2008)). This deacetylation activity is very specific, as SirT6 did not deacetylate the acetyl groups at H2A, H2B, H4 and other positions of H3 (Michishita et al., Nature, 452(7186): 492-496 (2008)). Except for telomeric chromatin, SirT6 deacetylates H3K9 at NF-κB target gene promoters, attenuating NF-κB signaling. These established enzymatic properties of SirT6 opened the window to decipher the cellular functions of SirT6. However, the kinetic and biochemistry properties about this enzyme are still lacking, especially from the standing point of enzymology.

The modulators of sirtuins have attracted a lot of attention and interest in recent years. For example, nicotinamide, a product in the sirtuin reaction, was found to inhibit the activity of yeast Sir2 and other sirtuins to some extent (Sauve et al., Annu. Rev. Biochem., 75: 435-465 (2006)). Resveratrol, a natural chemical found in grape seed, was shown to activate SirT1. These modulators play important roles in the cellular metabolism (Sauve et al., supra). Recently, SRT1720, a more potent activator of SirT1, was discovered after screening a large compound library and it has been shown to be useful in the improvement of whole-body glucose homeostasis and insulin sensitivity in adipose tissue, skeletal muscle and liver (Milne et al., Nature, 450(7170): 712-716 (2007)). To date, no modulators have been reported for SirT6.

BRIEF SUMMARY OF THE INVENTION

The invention provides a method of increasing a deacetylated activity of SIRT6, wherein the method comprises contacting the enzyme with an agent that binds SIRT6 and reduces the $K_m$ of SIRT6 for a substrate, thereby increasing the deacetylase activity of SIRT6.

Then invention also provides a compound of the formula (II):

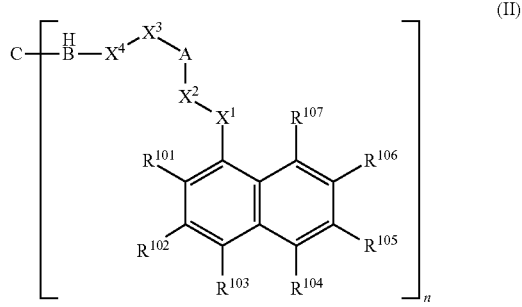

wherein $X^1$, $X^2$, $X^3$, and $X^4$ are independently selected from the group consisting of —O—, —C(=)—, —N($R^{108}$)—, —C($R^{109}$)$_2$—, —C(=S)—, —S—, —S(=O)—, and —S(=O)$_2$—, A is selected from the group consisting of alkylene, cycloalkylene, heterocycloalkylene, arylene, or heteroarylene optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfamoyl, sulfonyl, sulfoxido, and phosphate, B is a bond, alkyl, cycloalkyl, heterocycloalkyl, aryl, or heteroaryl optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfonyl, sulfoxido, or phosphate, C is absent or is selected from the group consisting of —NHC(=O)NH—, —C(=O)—, alkylene, and arylene, $R^{101}$, $R^{102}$, $R^{103}$, $R^{104}$, $R^{105}$, $R^{106}$, and $R^{107}$ are independently hydrogen, alkyl, cycloalkyl, heterocycloalkyl, aryl, or heteroaryl optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfonyl, sulfoxido, or phosphate, $R^{108}$ and $R^{109}$ are independently selected from the group consisting of hydrogen and $C_1$-$C_6$ alkyl, when C is absent, n is 1 and when C is —NHC(=O)NH—, —C(=O)—, alkylene, or arylene, n is 2, with the provisos that:
when C is arylene, $R^{103}$, $R^{105}$, and $R^{107}$ are not all sulfate;
when C is arylene substituted with alkyl, $R^{103}$ and $R^{105}$ are not both sulfate, and $R^{103}$ and $R^{107}$ are not both sulfate;
when B is a bond and C is —NHC(=O)NH—, $R^{105}$, and $R^{107}$ are not all sulfate, $R^{103}$ and $R^{105}$ are not both sulfate, and $R^{103}$ and $R^{107}$ are not both sulfate;
when A is 1,4-biphenylene, $R^{103}$, $R^{105}$, and $R^{107}$ are not all sulfate;
when A is 1,3-phenylene substituted with alkyl, alkoxy, halo, or carboxy, and B is amino-substituted phenyl, $R^{103}$, $R^{105}$, and $R^{107}$ are not all sulfate,
when A is 1,3-phenylene and B is amino-substituted phenyl, $R^{105}$ and $R^{107}$ are not both sulfate, and $R^{102}$ and $R^{107}$ are not both sulfate;
when A is 1,4-phenylene and B is amino-substituted phenyl, $R^{105}$ and $R^{107}$ are not both sulfate, and $R^{102}$ and $R^{107}$ are not both sulfate;
and when A and B are both 1,3-phenylene, $R^{103}$, $R^{105}$, and $R^{107}$ are not all sulfate.

The invention further provides a compound of the formula (III):

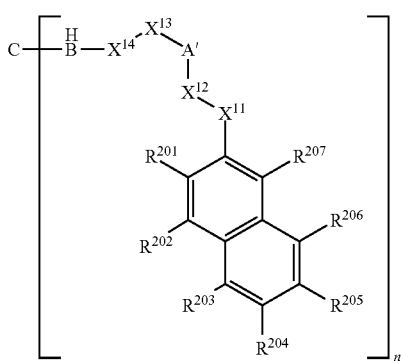

(III)

wherein $X^{11}$, $X^{12}$, $X^{13}$, and $X^{14}$ are independently selected from the group consisting of —O—, —C(=))—, —N($R^{208}$)—, —C($R^{209}$)$_2$—, —C(=S)—, —S—, —S(=O)—, and —S(=O)$_2$—, A is selected from the group consisting of alkylene, cycloalkylene, heterocycloalkylene, arylene, or heteroarylene optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfamoyl, sulfonyl, sulfoxido, and phosphate, B is selected from the group consisting of a bond, alkyl, cycloalkyl, heterocycloalkyl, aryl, or heteroaryl optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfonyl, sulfoxido, and phosphate, C is absent or is selected from the group consisting of —NHC(=O)NH—, —C(=O)—, alkylene, and arylene, $R^{201}$, $R^{202}$, $R^{203}$, $R^{204}$, $R^{205}$, $R^{206}$, and $R^{207}$ are independently hydrogen, alkyl, cycloalkyl, heterocycloalkyl, aryl, or heteroaryl optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfonyl, sulfoxido, or phosphate, $R^{208}$ and $R^{209}$ are hydrogen or $C_1$-$C_6$ alkyl, when C is absent, n is 1 and when C is —C(=O)—, —NHC(=O)NH—, alkylene, or arylene, n is 2, with the proviso that:
when C is arylene, $R^{202}$ and $R^{206}$ are not both sulfate.

BRIEF DESCRIPTION OF THE SEVERAL VIEWS OF THE DRAWING(S)

Figure 1A:
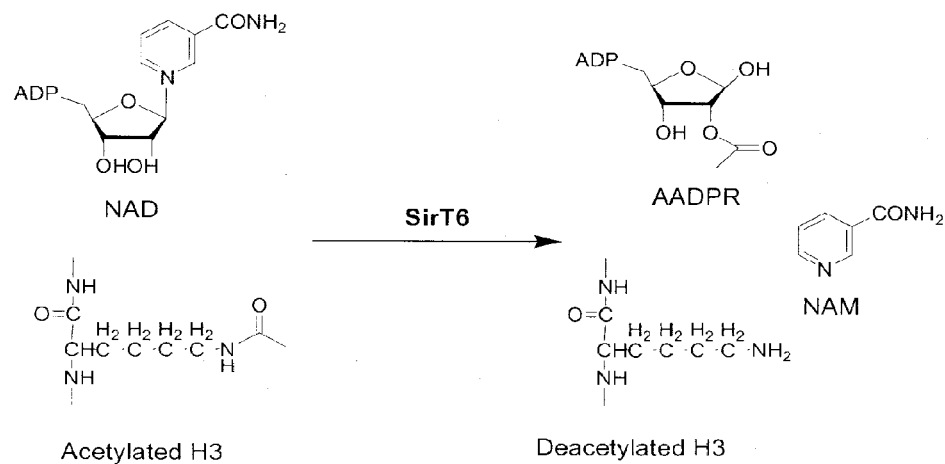
FIG. 1A depicts a SirT6 enzymatic reaction in which H3 and NAD act as substrates.
Figure 1B:
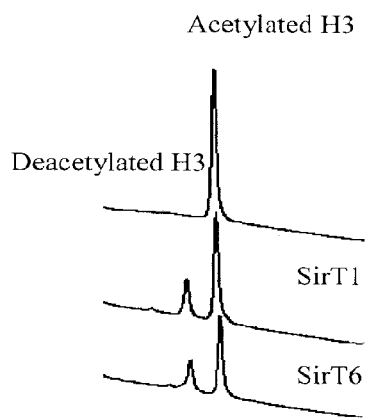
FIG. 1B depicts chromatography of deacetylated H3 and acetylated H3 in the enzymatic reactions of SirT6 and SirT1. Peptides were eluted by gradient (0-30%) acetonitrile in 0.1% TFA using a C18 column.
Figure 1C:
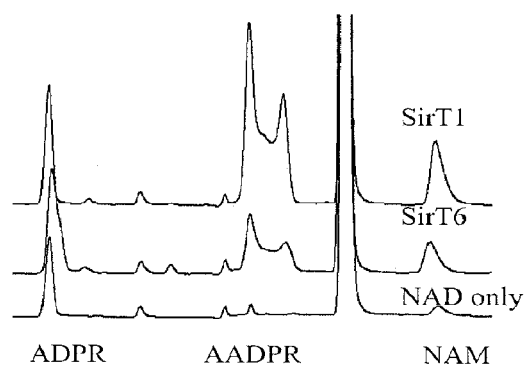

FIG. 1C depicts chromatography of AADPR, ADPR and NAM formed in the enzymatic reaction of SirT6. The substrates and the products were separated by 20% ammonium acetate using a C18 column. AADPR isomers were eluted together before NAD and shown as a fork-like peak.

Figure 2A:
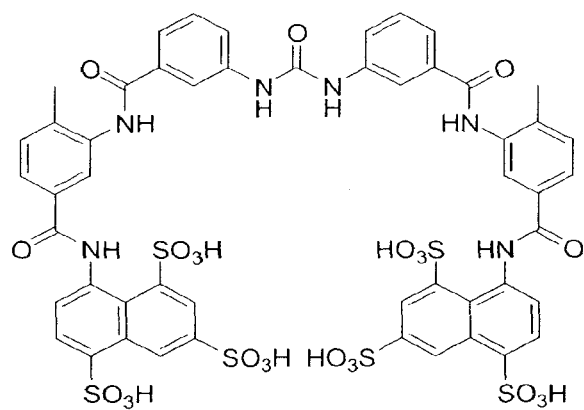

FIG. 2A depicts the structure of suramin.

Figure 2B:
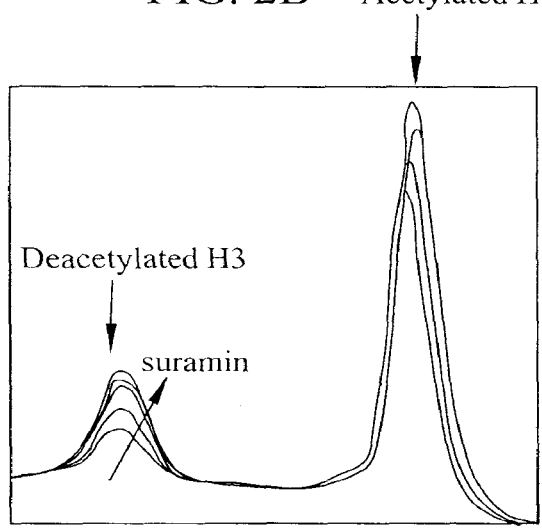

FIG. 2B shows that the peak of the deacetylated H3 increases with suramin in the SirT6 enzymatic reaction.

Figure 2C:
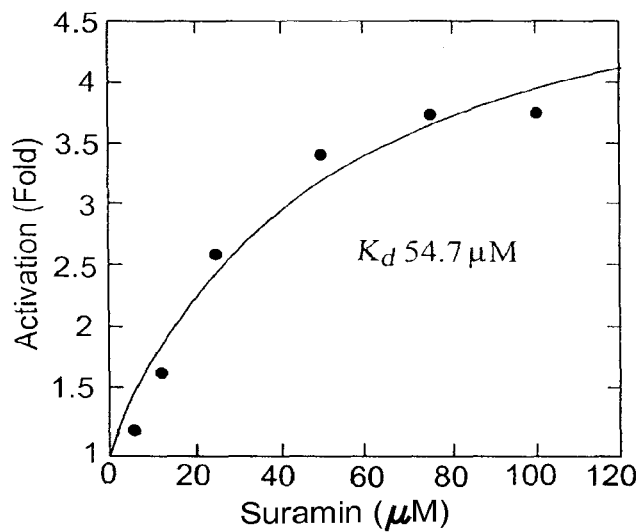

FIG. 2C depicts the determination of $K_d$ of suramin for activation of SirT6. The enzymatic reaction was carried out in the solution involving 800 μM NAD, 300 μM H3, 12 μM SirT6 and different concentrations of suramin. After 2 hours incubation at 37° C., the deacetylated H3 was separated from H3 by gradient (0~30%) acetonitrile in 0.1% TFA using a C18 column, and analyzed by integrating its area at 215 nm wavelength. The quantified data were fit into the equation: Activation (Fold)=1+m*x/($K_d$+x), and $K_d$ was determined as 54.7 µM.

Figure 3:
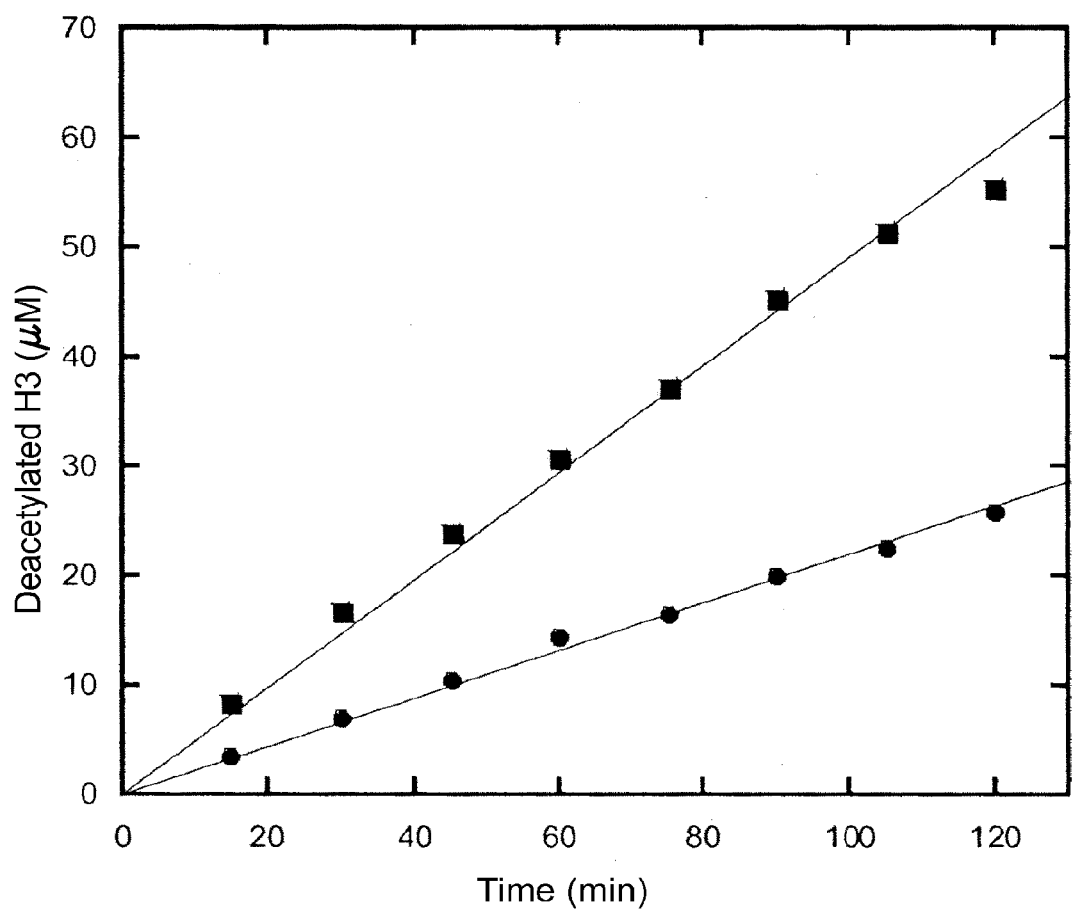

FIG. 3 shows that suramin activation was not due to stabilization of SirT6. The enzymatic reaction was carried out in the solution involving 800 µM NAD, 500 µM H3, 12 µM SirT6 and 50 µM suramin. After 2 hours incubation at 37° C., the deacetylated H3 and acetylated H3 at different time points were separated by gradient (0~30%) acetonitrile in 0.1% TFA using a C18 column, and analyzed by integrating its area at 215 nm wavelength. The quantified data were linearly regressed by KaleidaGraph. No suramin (solid circle); 50 µM suramin (solid rectangular).

Figure 4A:
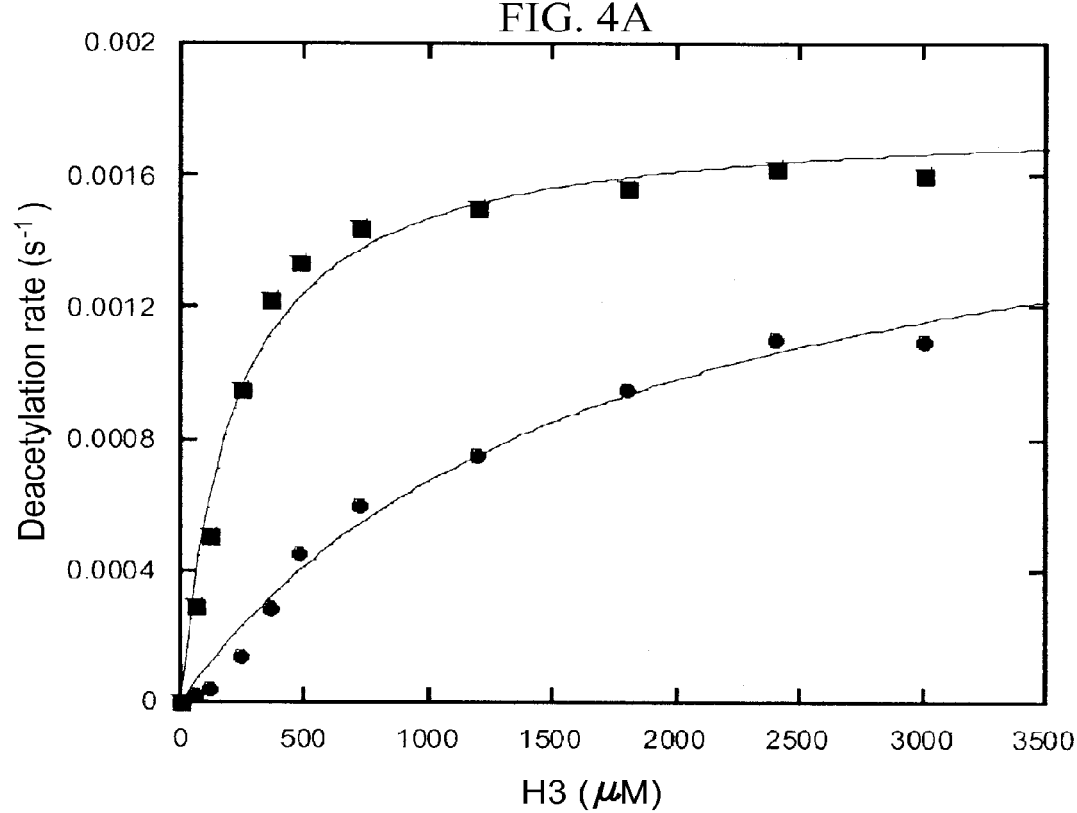
Figure 4B:
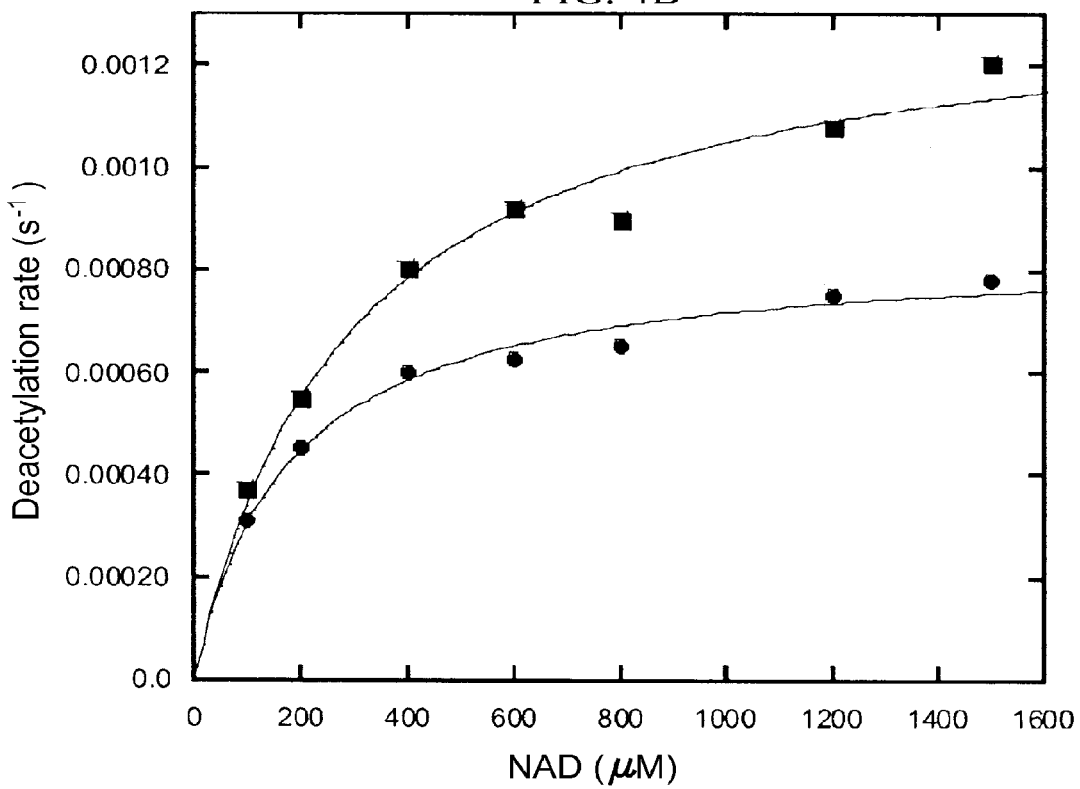

FIGS. 4A and 4B show that suramin dramatically decreased $K_m$ of H3 of SirT6, but only marginally affected $K_m$ of NAD of SirT6. FIG. 4A shows the determination of $K_m$ of H3 with and without suramin. The enzymatic reaction was carried out in the solution involving 800 µM NAD, 10 µM SirT6, and different concentration of H3 with 50 µM suramin as indicated. After 2 hours incubation at 37° C., AADPR in the reaction was separated from other chemicals by HPLC using 20 mM ammonium acetate and analyzed by integrating its area at 260 nm wavelength. The quantified data were fit into Michaelis-Menten equation to get $K_m$ of H3. No suramin (solid circle), $K_m$=1565.2 µM; 50 µM suramin (solid rectangular), $K_m$=213.5 µM. FIG. 4B shows the determination of $K_m$ of NAD with and without suramin. The enzymatic reaction was carried out in the solution involving 1 mM H3, 10 µM SirT6 and different concentration of NAD with 50 µM suramin as indicated. After 2 hours incubation at 37° C., AADPR in the reaction was separated and analyzed by integrating its area at 260 nm wavelength in the chromatograph. The quantified data were fit into Michaelis-Menten equation to get $K_m$ of NAD. No suramin (solid circle), $K_m$=177.8 µM; 50 µM suramin (solid rectangular), $K_m$=293.5 µM.

Figure 5A:
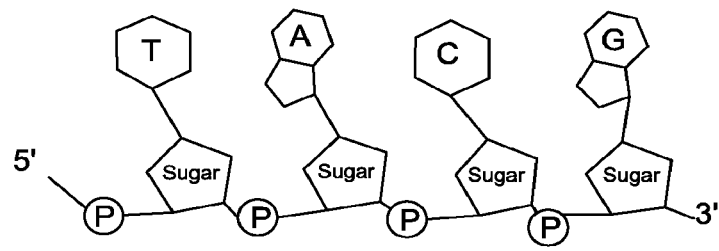
Figure 5B:
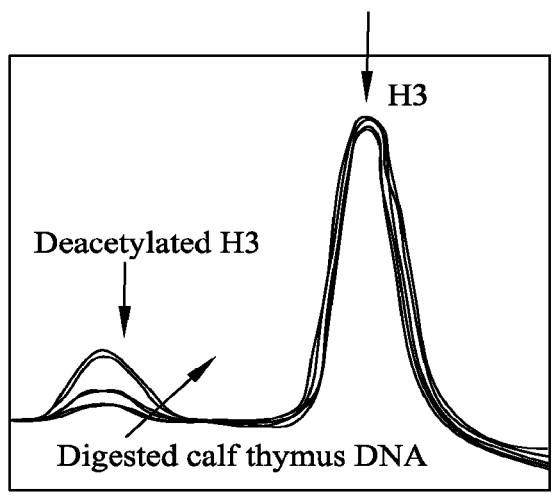
Figure 5C:
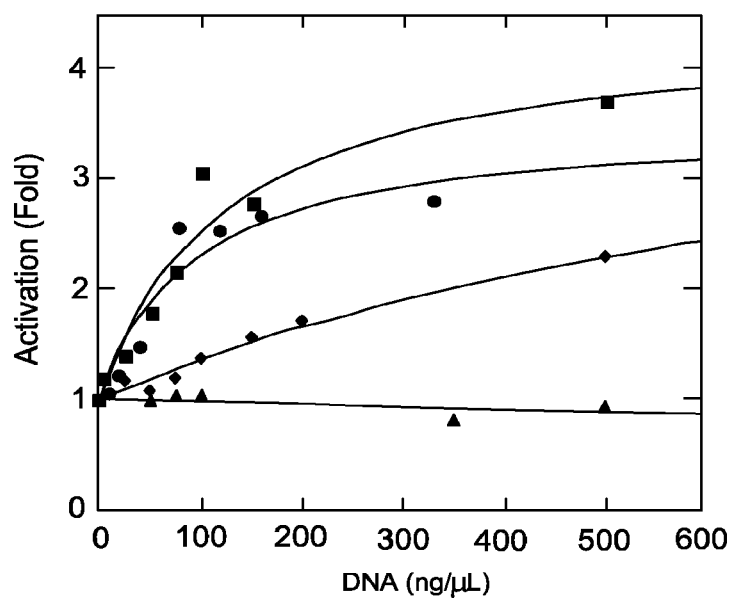

FIG. 5 shows that DNA activated the deacetylation activity of SirT6. FIG. 5A depicts a schematic of DNA structure. FIG. 5B shows that the peak of the deacetylated H3 increased with the concentration of DNA in the reaction. FIG. 5C shows that activation of SirT6 by different DNA, including a single strain DNA (ssDNA), the digested calf thymus DNA, the plasmid of pSTBlue, and a double strain DNA (dsDNA). The enzymatic reaction was carried out in the solution involving 800 µM NAD, 480 µM H3, 10 µM SirT6 and different concentrations of DNA. After 2 hours incubation at 37° C., either the deacetylated H3 was separated from H3 in the reaction containing the digested calf thymus DNA or AADPR was separated from other components in the reaction containing ssDNA, the plasmid, or dsDNA. The quantified data were fit into the equation: Activation (fold)=1+m*x/($K_d$+x). ssDNA (solid rectangular), $K_d$ 127.7 ng/µl; Digested DNA (solid circle), $K_d$ 94.8 ng/µl; pSTBlue (solid diamond), $K_d$ (947 ng/µl) dsDNA (solid triangle), $K_d$>10 mM.

Figure 6A:
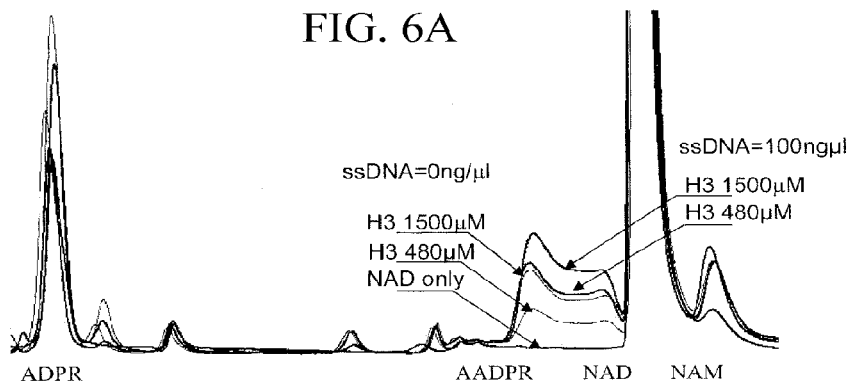
Figure 6B:
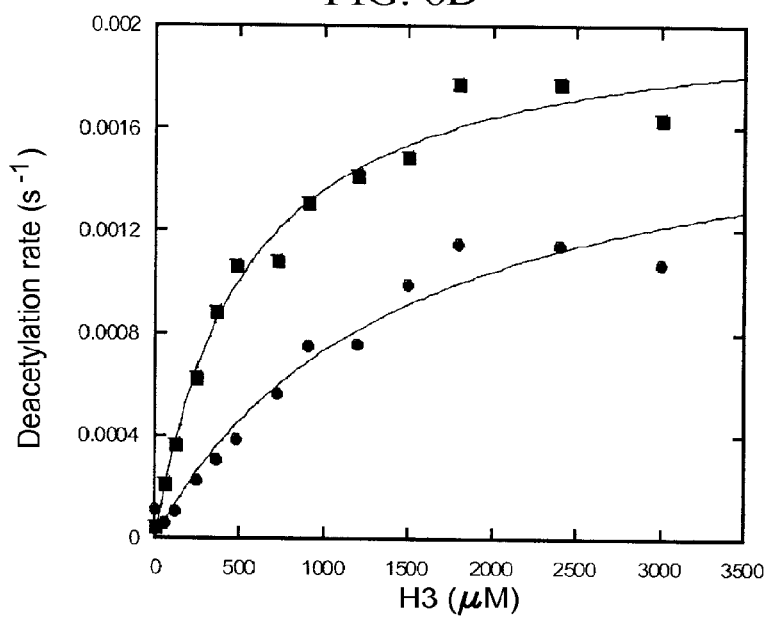
Figure 6C:
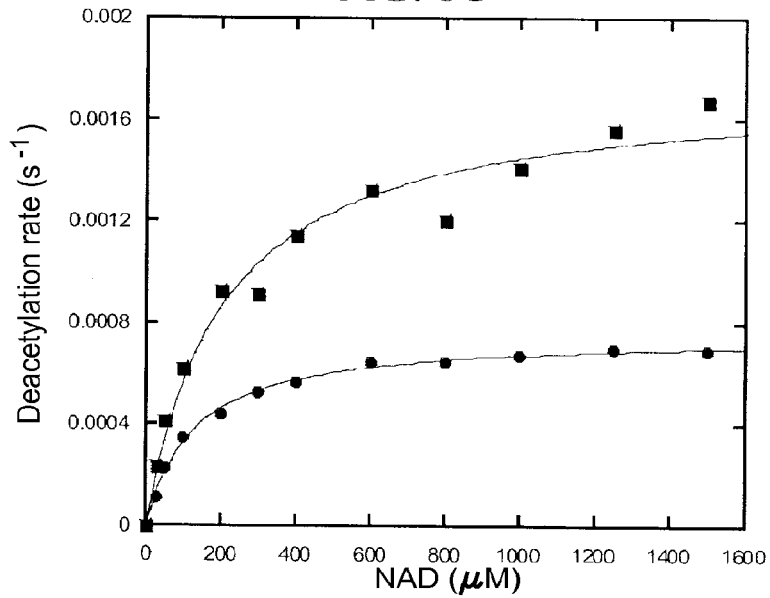

FIG. 6 shows that DNA decreased $K_m$ of H3 of SirT6. FIG. 6A depicts chromatography of the SirT6 enzymatic reaction activated by ssDNA. FIG. 6B shows that ssDNA decreased $K_m$ of H3 of SirT6. The enzymatic reaction was carried out in the solution involving 800 µM NAD, 10 µM SirT6, and different concentrations of H3 with 100 ng/µl ssDNA as indicated. FIG. 6C shows that ssDNA marginally affected $K_m$ of NAD. The enzymatic reaction was carried out in the solution involving 10 µM SirT6, 1 mM H3, and different concentrations of NAD with 100 ng/µl ssDNA as indicated. All the reactions were incubated at 37° C. for 2 hours and AADPR in the reaction was separated from other chemicals by HPLC using 20 mM ammonium acetate and analyzed by integrating its area at 260 nm wavelength. The quantified data were fit into Michaelis-Menten equation to get $K_m$ of H3. Without ssDNA (solid circle), $K_m$ of H3=1565.2 $K_m$ of NAD=128.0 µM; with 100 ng/µl ssDNA (solid rectangle), $K_m$ of H3=523.3 µM, $K_m$ of NAD=204.7 µM.

Figure 7A:
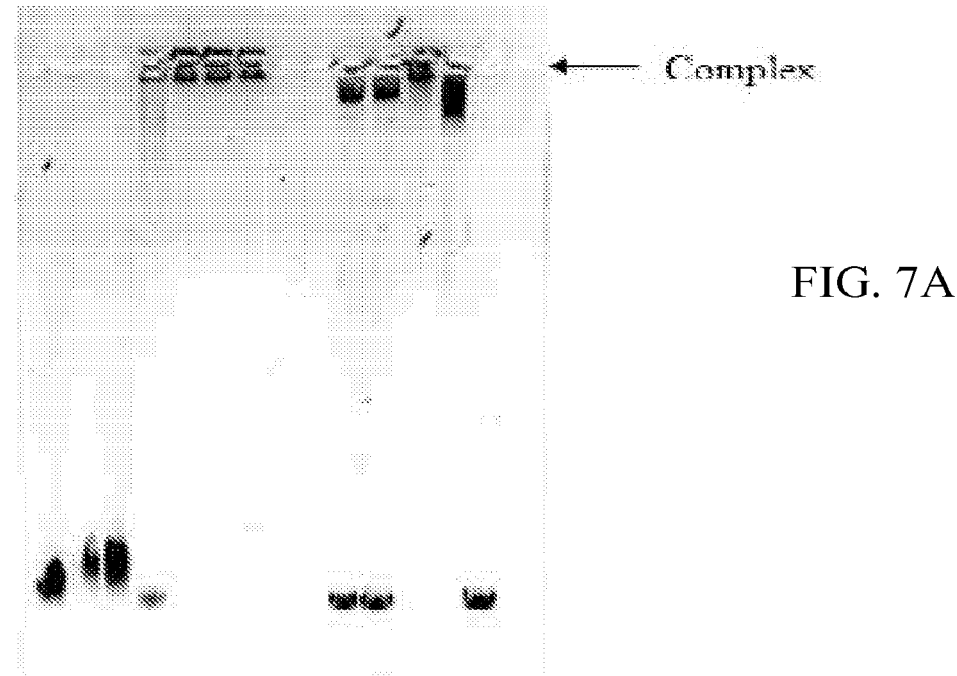
Figure 7B:
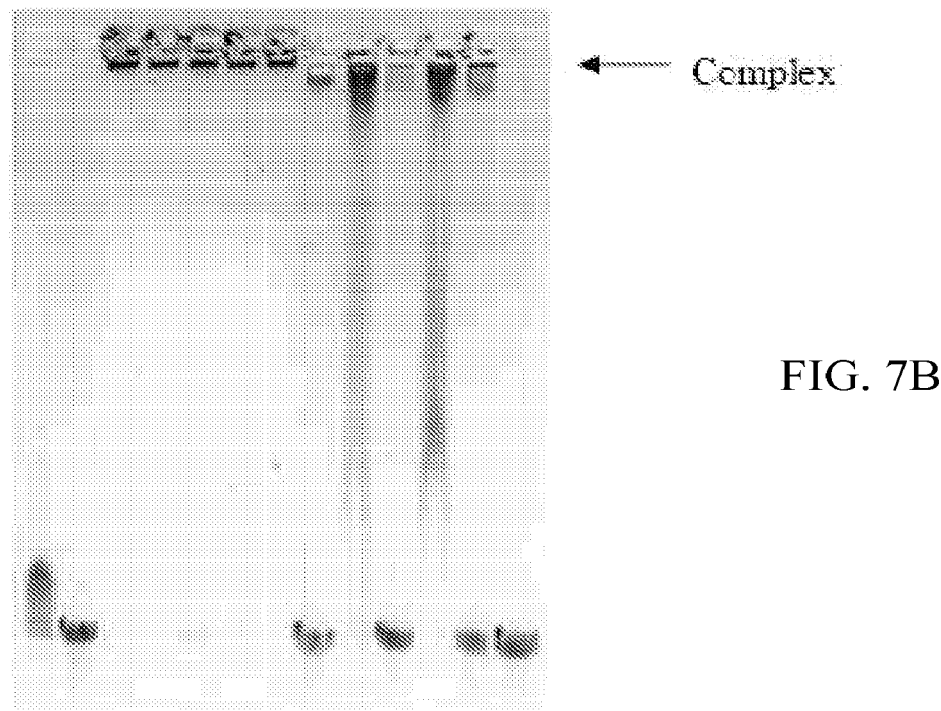

FIG. 7 shows that the binding of DNA to SirT6 was strengthened by H3, but not by H4. FIG. 7A shows that the association of DNA to SirT6 was strengthened by H3 D, but weakened by suramin. Lane 1, DNA+NAD; Lane 2, DnA+H3; Lane 3, DNA+NAD+H3; Lane 4, DNA+SirT6; Lane 5, DNA+NAD+SirT6; Lane 6, DNA+H3+SirT6; Lane 7, DNA+NAD+H3+SirT6; Lane 8, DNA+SirT6+1 mM suramin; Lane 9, DNA+NAD+SirT6+1 mM suramin; Lane 10, DNA+H3+SirT6+1 mM suramin; Lane 11, DNA+NAD+H3+SirT6+1 mM suramin; Lane 12, DNA only. FIG. 7B shows that the association of DNA to SirT6 was not strengthened by H4, which is not the substrate of SirT6. Lane 1, DNA+H3; Lane 2, DNA+H4; Lane 3, DNA+SirT6; Lane 4, DNA+H3+SirT6; Lane 5, DNA+H4+SirT6; Lane 6, DNA+NAD+H3+SirT6; Lane 7, DNA+NAD+H4+SirT6; Lane 8, DNA+SirT6+1 mM suramin; Lane 9, DNA+H3+SirT6+1 mM suramin; Lane 10, DNA+H4+SirT6+1 mM suramin; Lane 11, DNA+NAD+H3+SirT6+1 mM suramin; Lane 12, DNA+NAD+H4+SirT6+1 mM suramin; Lane 13, DNA only. 6 µl of each sample involving 50 ng/µl linearized pSTBlue plasmid, 800 µM NAD, 10 µM SirT6, 480 µM H3/H4, and/or 1 mM suramin were loaded to 0.6% native agarose gel containing ethidium bromide and ran at 100 V for one and half hours. DNA bound to SirT6 stayed in the wells and free DNA ran to the bottom of the gel. The top arrow indicated the large complex formed by DNA and SirT6.

Figure 8A:
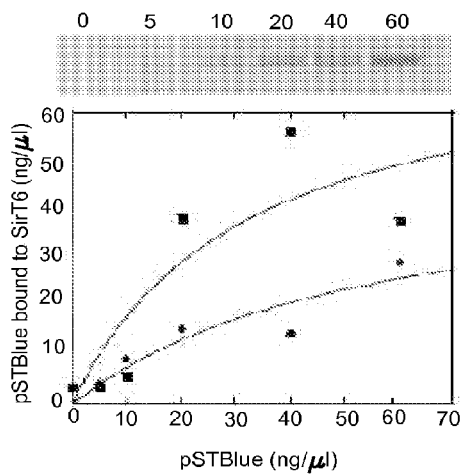
Figure 8B:
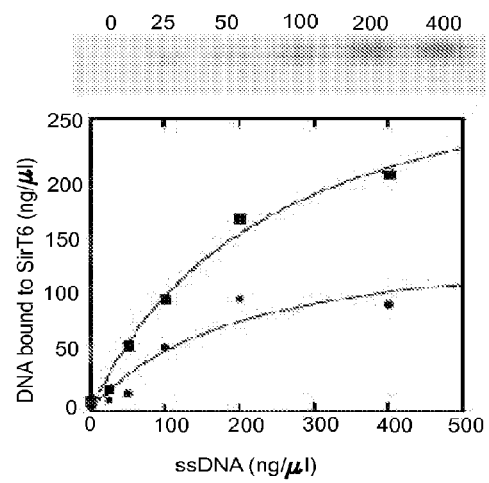
Figure 8C:
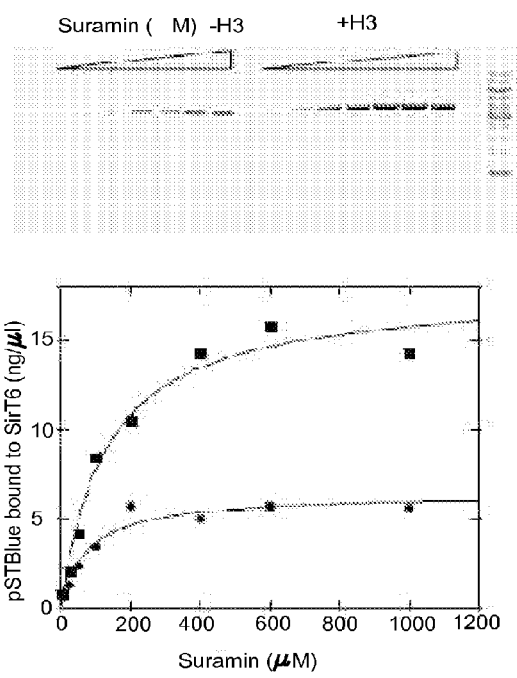
Figure 8D:
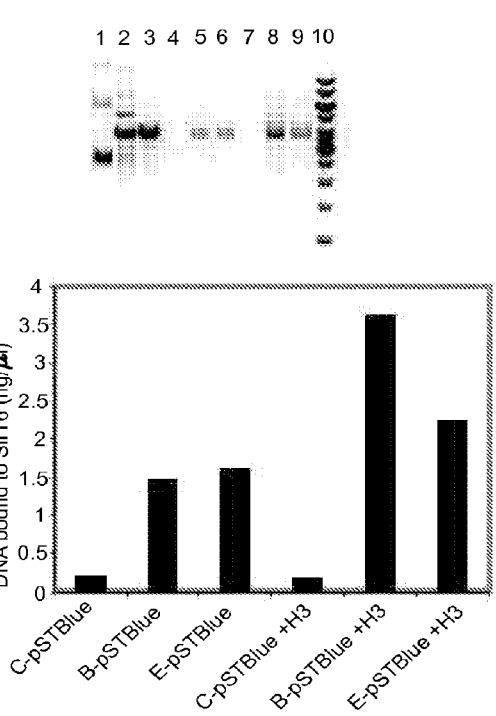

FIG. 8A shows that the level of linearized DNA bound to SirT6 was increased in the presence of H3 peptide. The linearized DNA was incubated with SirT6 and Ni-NTA resin. The resin was washed as described in Materials and Methods, and the complex of SirT6-DNA was dissociated by 1 mM suramin. DNA was stained with ethidium bromide and exposed to UV for image as shown in the Figure. The parallel experiments were done in the presence of 500 uM H3 peptide. DNA bound to SirT6 was quantified and fit to Michaelis-Menten equation to get $K_d$ of DNA binding to the enzyme. In the absence of H3, $K_d$ 53.8 ng/µl, $V_{max}$ 48.9 ng/µl; in the presence of H3, $K_d$ 31.2 ng/µl, $V_{max}$ 74.6 ng/µl. FIG. 8B shows that the level of ssDNA bound to SirT6 was increased in the presence of H3 peptide. The single stranded DNA was incubated with SirT6 and Ni-NTA resin. The resin was washed and the complex of SirT6-ssDNA was dissociated by 1 mM suramin. DNA was stained with ethidium bromide and exposed to UV for image as shown in the Figure. The parallel experiments were done in the presence of 500 uM H3 peptide. In the absence of H3, $K_d$ 195.5 ng/µl, $V_{max}$ 151.7 ng/µl; in the presence of H3, $K_d$ 238.8 ng/µl, $V_{max}$ 333.5 ng/µl. FIG. 8C shows that suramin competed with the binding of linearized DNA. The linearized DNA was incubated with SirT6 and Ni-NTA resin with or without H3 peptide. After washing, the resin was incubated with different concentration of surmain. The dissociated DNA was quantified by gel electrophoresis. In the absence of H3, $K_d$ 72.4 µM, $V_{max}$ 6.37 ng/µl; in the presence of H3, $K_d$ 128.9 µM, $V_{max}$ 17.8 ng/µl. FIG. 8D shows that circular DNA could not bind to SirT6. pSTBlue uncut, or cut with BamHI or EcoRV was incubated with SirT6 and Ni-NTA without or with 1 mM H3 peptide. After the resin was washed, DNA was dissociated with 1 mM suramin and quantified by gel electrophoresis. Lane 1, 150 ng circular pSTBlue (C-pSTBlue); Lane 2, 150 ng pSTBlue cut with BamHI (B-pSTBlue); Lane 3, 150 ng pSTBlue cut with EcoRV (E-pSTBlue); Lane 4, circular pSTBlue bound to SirT6; Lane 5, pSTBlue cut with BamHI bound to SirT6; Lane 6, pSTBlue cut with EcoRV bound to SirT6; Lane 7, circular pSTBlue bound to SirT6 in the presence of H3; Lane 8, pSTBlue cut with BamHI bound to SirT6 in the presence of H3; Lane 9, pSTBlue cut with EcoRV bound to SirT6 in the presence of H3; Lane 10, DNA ladder.

Figure 9:
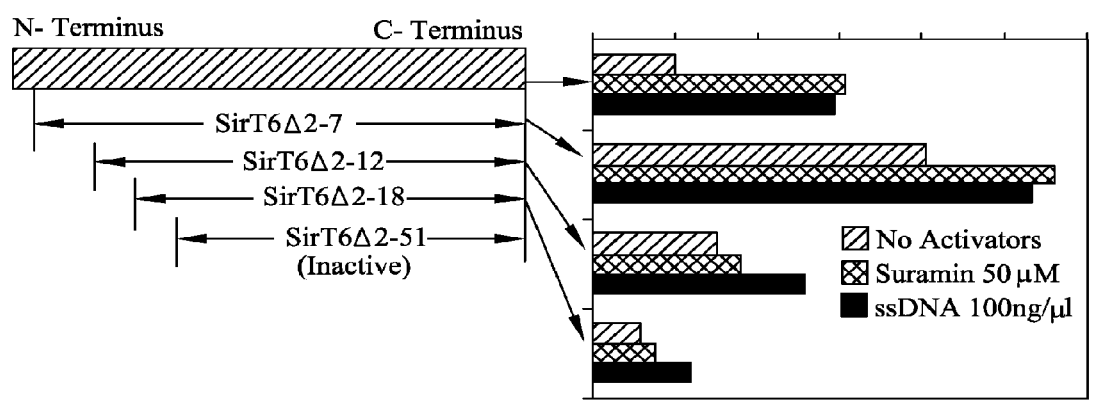

FIG. 9 shows that the N-terminus of SirT6 is important for suramin and DNA activation. The enzymatic reaction was carried out in the solution involving 800 µM NAD, 480 µM H3, 10 µM enzyme with 50 µM suramin or 100 ng/µl single stranded DNA as indicated. The deacetylation rate of different truncated SirT6 was normalized to the rate of full length SirT6 for the comparison. As shown on right, the deletion of N terminal 17 amino acids caused the lost of activation by suramin and DNA.

Figure 10A:
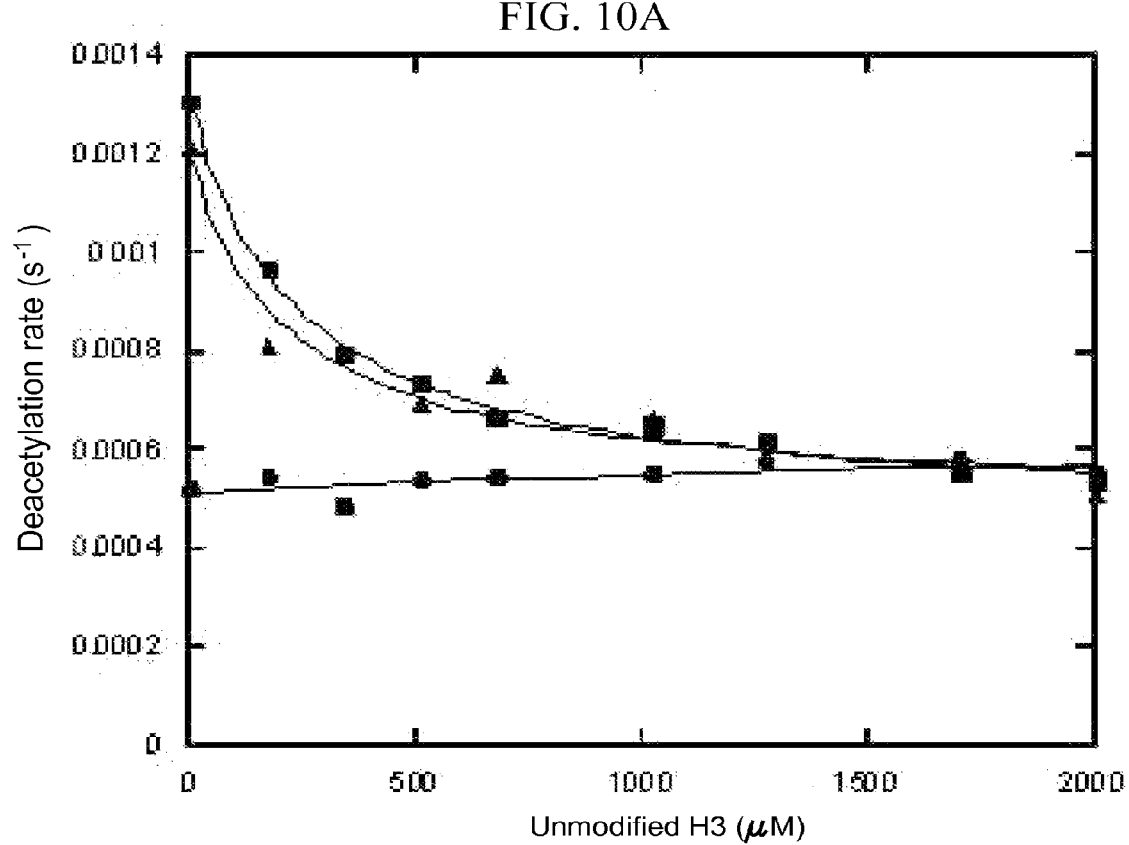
Figure 10B:
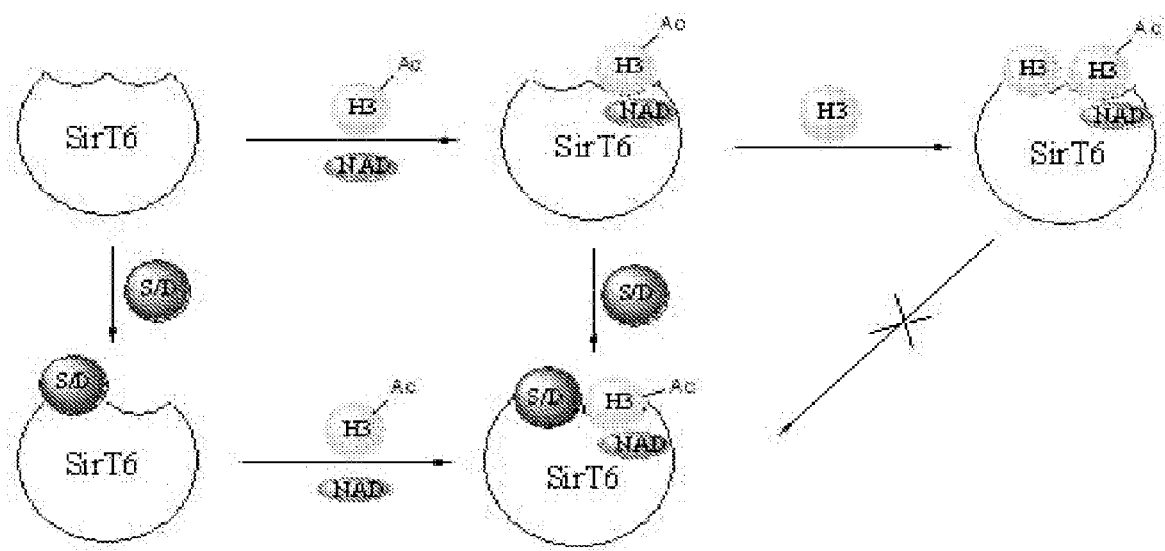

FIG. 10 shows that unmodified H3 inhibited the activation from DNA and from suramin. FIG. 10A shows that the unmodified H3 inhibited the activation from DNA and from suramin. The enzymatic reaction was carried out in the solution involving 800 µM NAD, 10 µM SirT6, 480 µM H3 and different concentration of unmodified H3 (without acetyl groups) with 100 ng/µl ssDNA or 50 µM suramin as indicated. The reaction was incubated at 37° C. for 2 hours and then quenched with 10% TFA. AADPR in the reaction was separated from other chemicals by HPLC using 20 mM ammonium acetate and analyzed by integrating its area at 260 nm wavelength. The quantified data were fit into the equation $v=m_1-m_2*x/(K_i+x)$ to get $K_i$ of deacetylated H3. No ssDNA (solid circle); 100 ng/µl ssDNA (solid rectangle), $K_i$ 240.4 µM; 50 µM suramin (solid triangle), $K_i$ 213.9 µM. FIG. 10B illustrates a schematic of SirT6 activation. Suramin or DNA induced the conformation change of SirT6, leading to the strengthened binding of H3 to SirT6 and the decrease in $K_m$ of H3; on the other hand, the binding of H3 to SirT6 assisted the binding of suramin/DNA to SirT6, which is tighter than that when H3 is absent. The unmodified H3 competed with the binding site of suramin/DNA, leading to the disappearance of activation by them. S/D, suramin or DNA.

Figure 11:
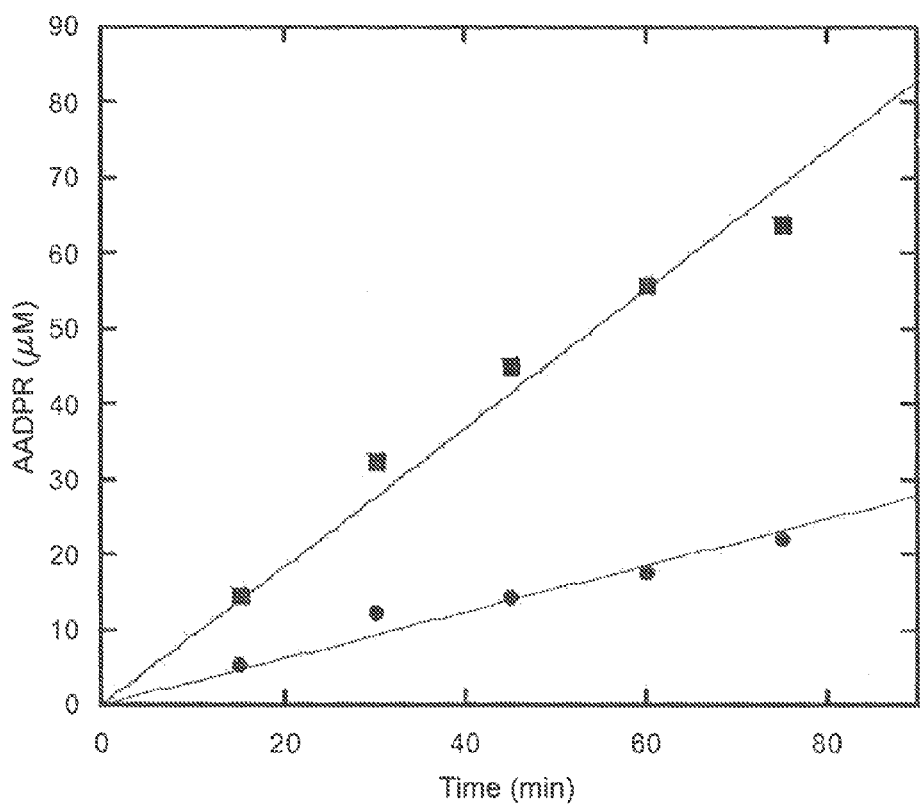

FIG. 11 shows that SirT6 was stable in the presence and absence of ssDNA. The enzymatic reaction was carried out in the solution involving 800 µM NAD, 10 µM SirT6, 480 µM H3 and 100 ng/µl ssDNA as indicated. The reaction was incubated at 37° C. for 2 hours and the samples were taken from the reaction at each time point. After quenching with 10% TFA, AADPR in the reaction was separated from other chemicals by HPLC using 20 mM ammonium acetate and analyzed by integrating its area at 260 nm wavelength. The quantified data were linearly regressed by KaleidaGraph. No ssDNA (solid circle); 100 ng/µl ssDNA (solid rectangular).

Figure 12A:
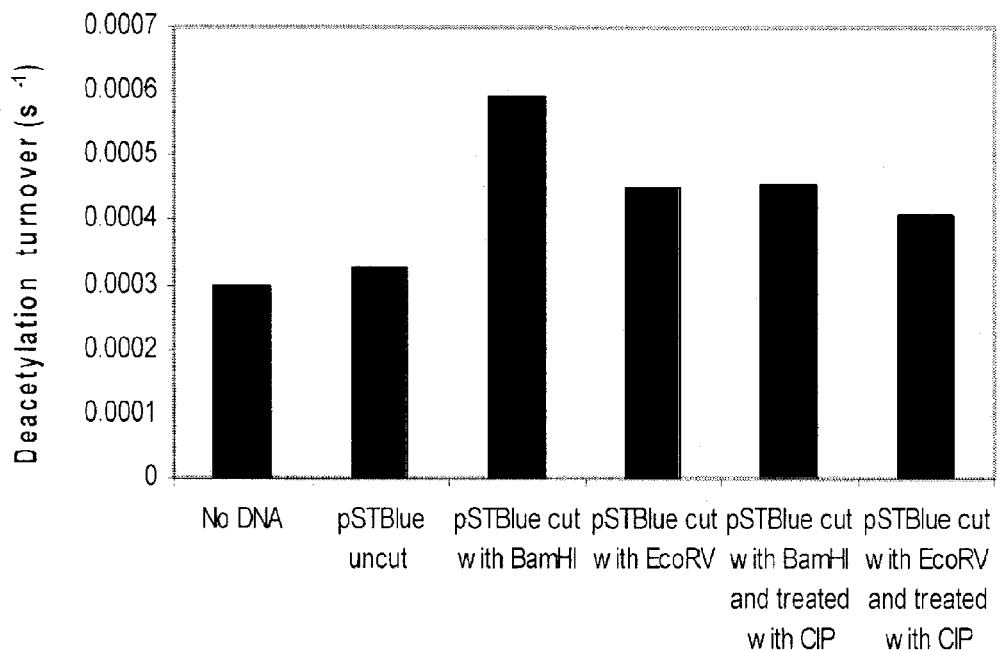
Figure 12B:
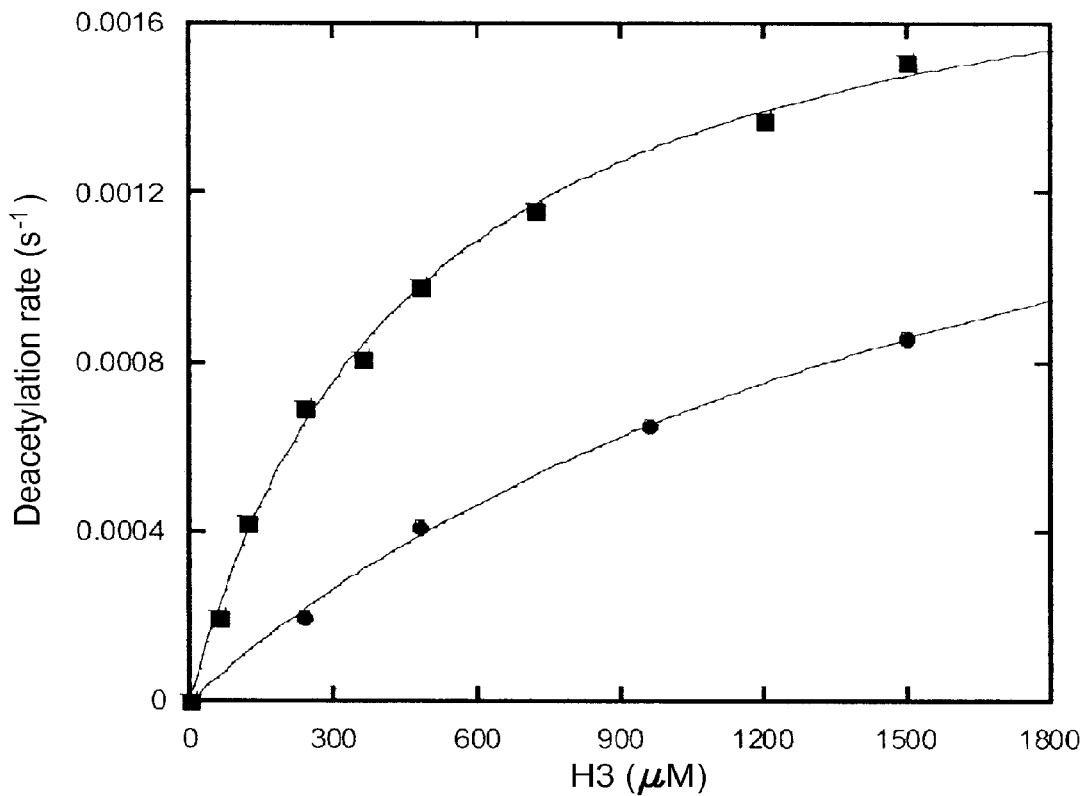

FIG. 12 shows that the linearized pSTBlue and 1 kb ladder activated the deacetylation activity of SirT6. FIG. 12A shows that the linearized pSTBlue activated the deacetylation activity of SirT6. The plasmid pSTBlue was digested with BamHI and EcoRV and purified by GENECLEAN™ III kit. The enzymatic reaction was carried out in the solution involving 800 µM NAD, 10 µM SirT6, 50 ng/µl pSTBlue cut either with BamHI, EcoRV or further treated with alkaline phosphatase, and 480 µM H3 at 37° C. for 2 hours and then quenched with 10% TFA. AADPR in the reaction was separated from other chemicals by HPLC using 20 mM ammonium acetate and analyzed by integrating its area at 260 nm wavelength. FIG. 12B shows that the 1 kb DNA ladder (Invitrogen) activated the deacetylation activity of SirT6. The enzymatic reaction was carried out in the solution involving 800 µM NAD, 10 µM SirT6, 100 ng/µl 1 kb DNA ladder, and H3 with different concentrations at 37° C. for 2 hours. The AADPR was separated by HPLC and the quantified data were fit into Michaelis-Menten equation to get $K_m$ of H3. Without 1 kb DNA ladder (solid circle), $K_m$=1565.2 µM; with 100 ng/ul 1 kb DNA ladder (solid rectangular), $K_m$=471.8 µM.

Figure 13:
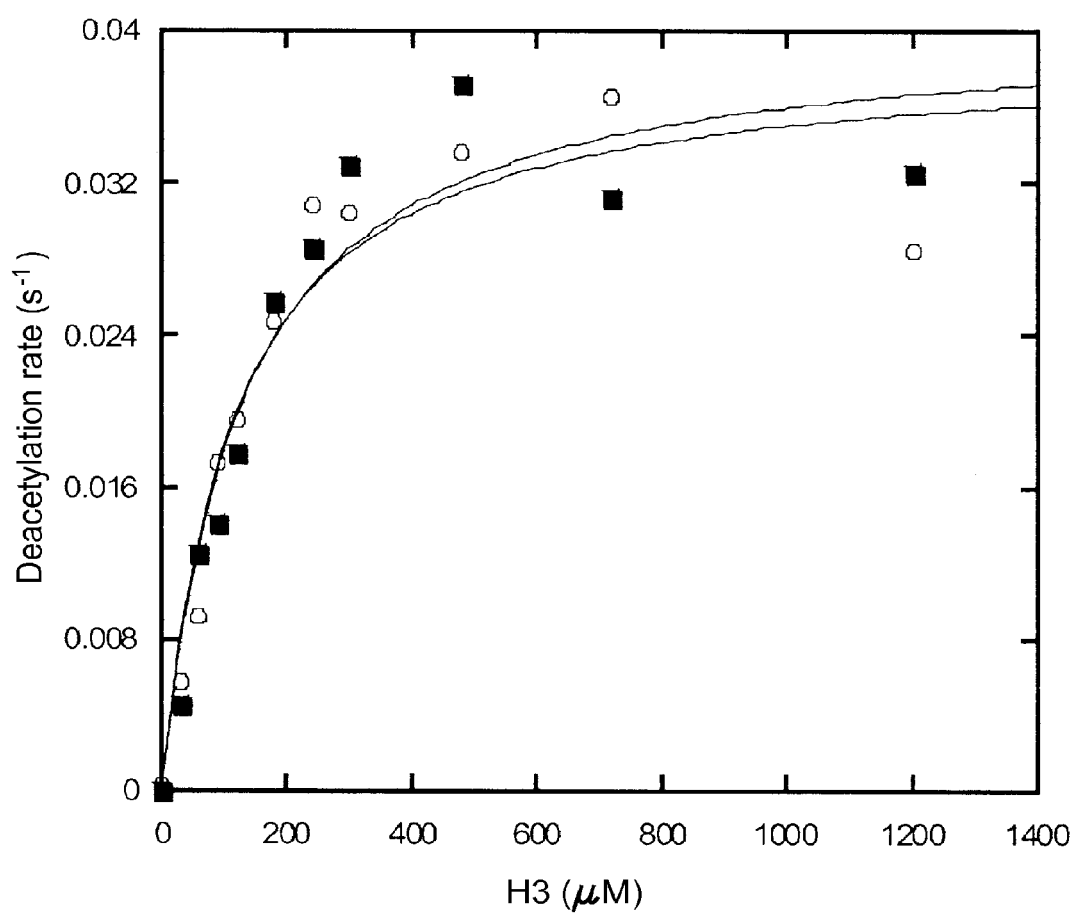

FIG. 13 shows that the deacetylation activity of SirT1 was not activated by DNA. The enzymatic reaction was carried out in the solution involving 800 µM NAD, 2 µm SirT1, 100 ng/µl ssDNA (Integrated DNA Technologies) as indicated and H3 with different concentrations. The reaction was incubated at 37° C. for 2 hours and then quenched with 10% TFA. AADPR in the reaction was separated from other chemicals by HPLC using 20 mM ammonium acetate and analyzed by integrating its area at 260 nm wavelength. The quantified data were fit into Michaelis-Menten equation to get $K_m$ of H3. Without ssDNA (blank circle), $K_m$=112.2 µM; with 100 ng/ul ssDNA (solid rectangular), $K_m$=124.5 µM.

Figure 14A:
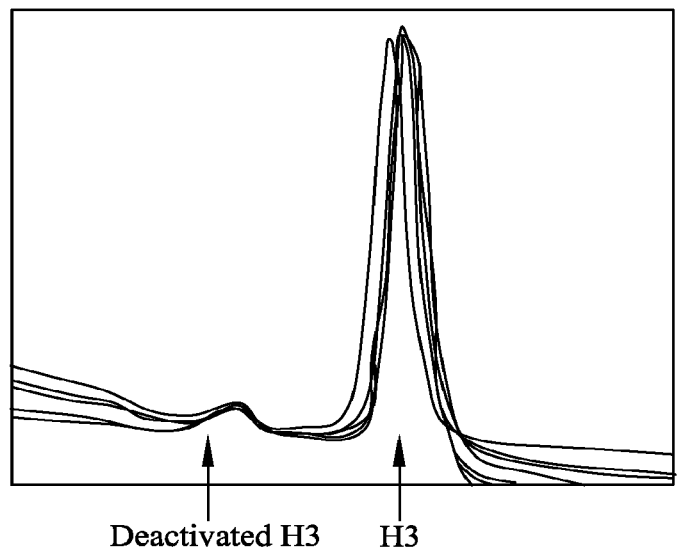
Figure 14B:
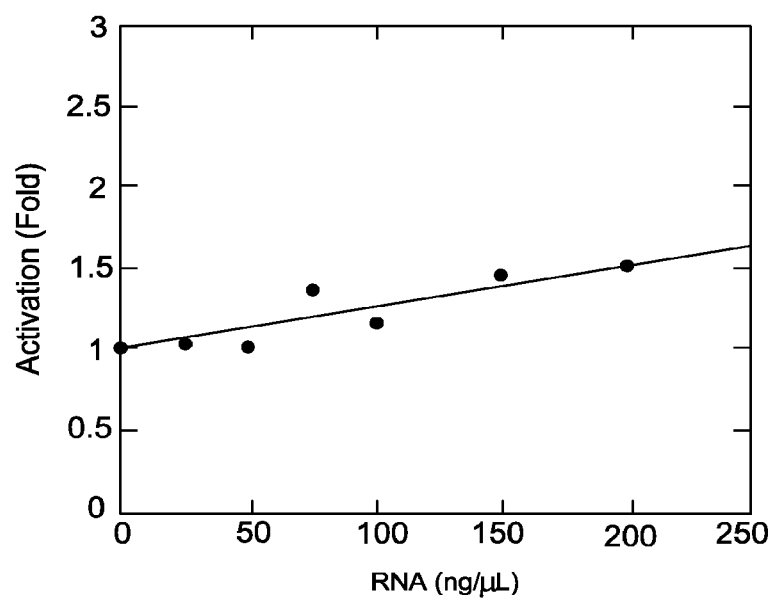

FIG. 14 shows that the deacetylation activity of SirT6 was not activated by RNA. The enzymatic reaction was carried out in the solution involving 800 µM NAD, 6 µM SirT6, 500 µM H3 with different concentration of yeast RNA (Sigma-Aldrich). The reaction was incubated at 37° C. for 2 hours and then quenched with 10% TFA. The deacetylated H3 was separated from other chemicals by HPLC using gradient 0.1% TFA-acetonitrile, and analyzed by integrating its area at 215 nm wavelength.

Figure 15A:
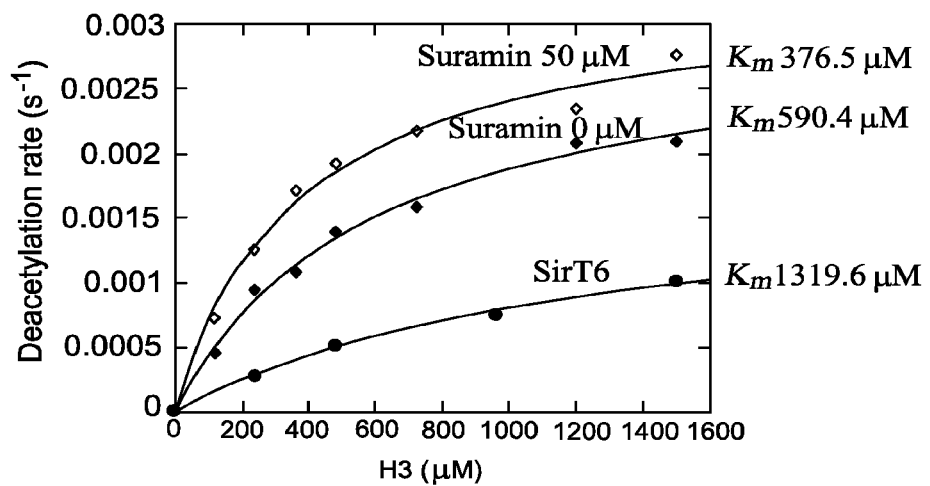
Figure 15B:
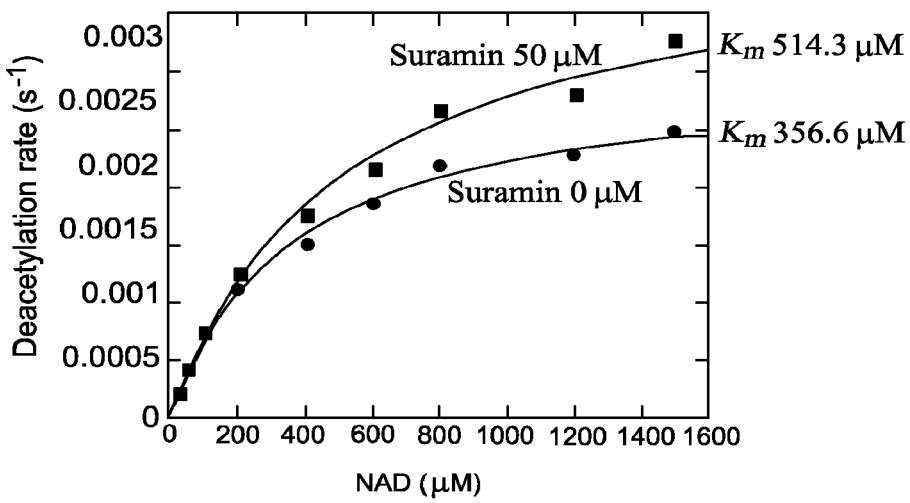
Figure 15C:
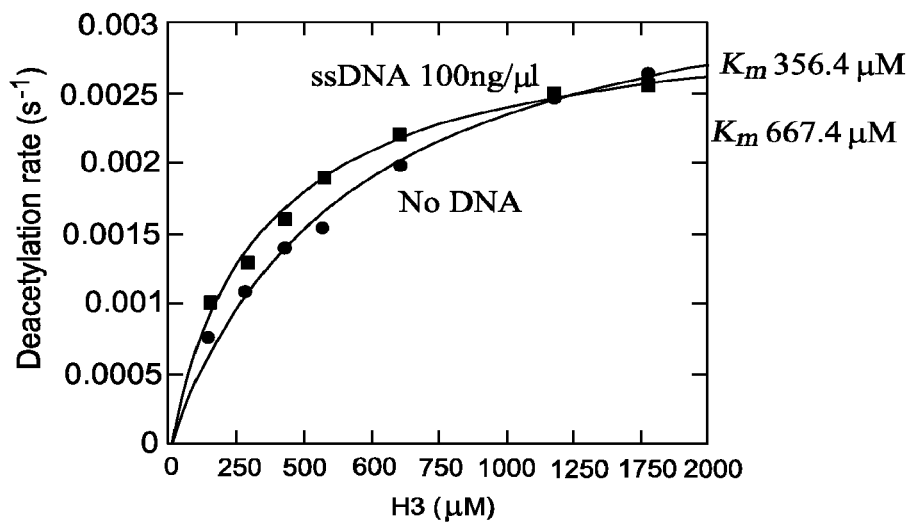

FIG. 15 illustrates $K_m$ of H3, $K_m$ of NAD of SirT6Δ2-7 in the presence of suramin or ssDNA.

Figure 16A:
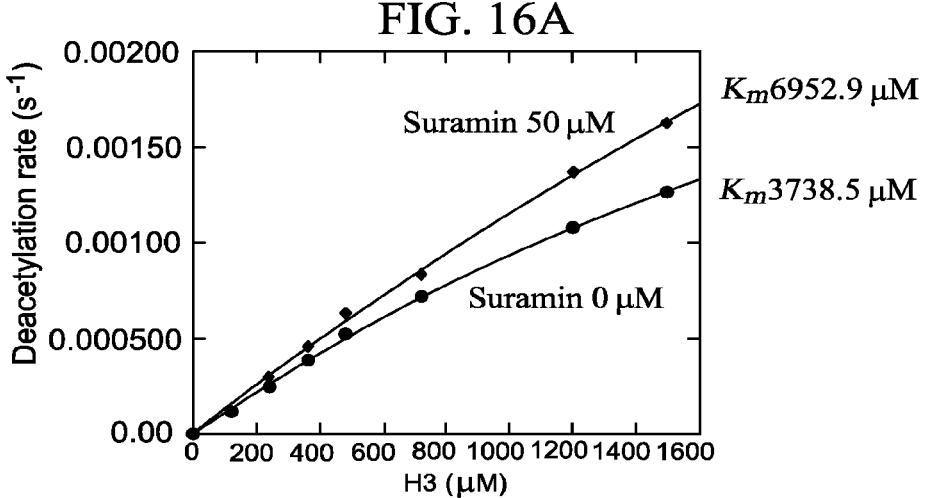
Figure 16B:
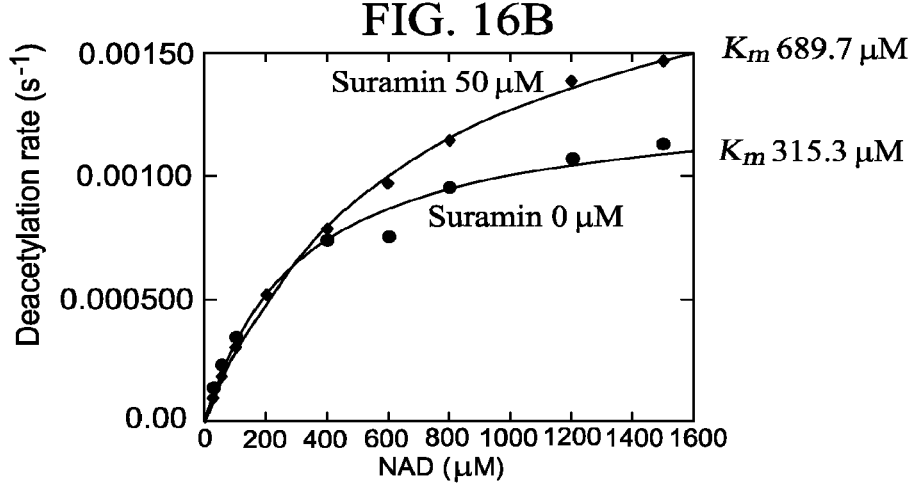
Figure 16C:
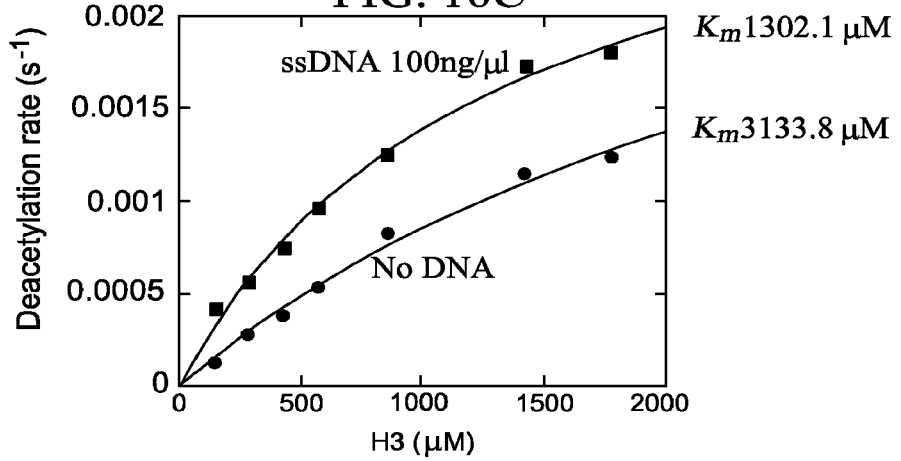

FIG. 16 illustrates $K_m$ of H3, $K_m$ of NAD of SirT6Δ2-12 in the presence of suramin or ssDNA.

Figure 17A:
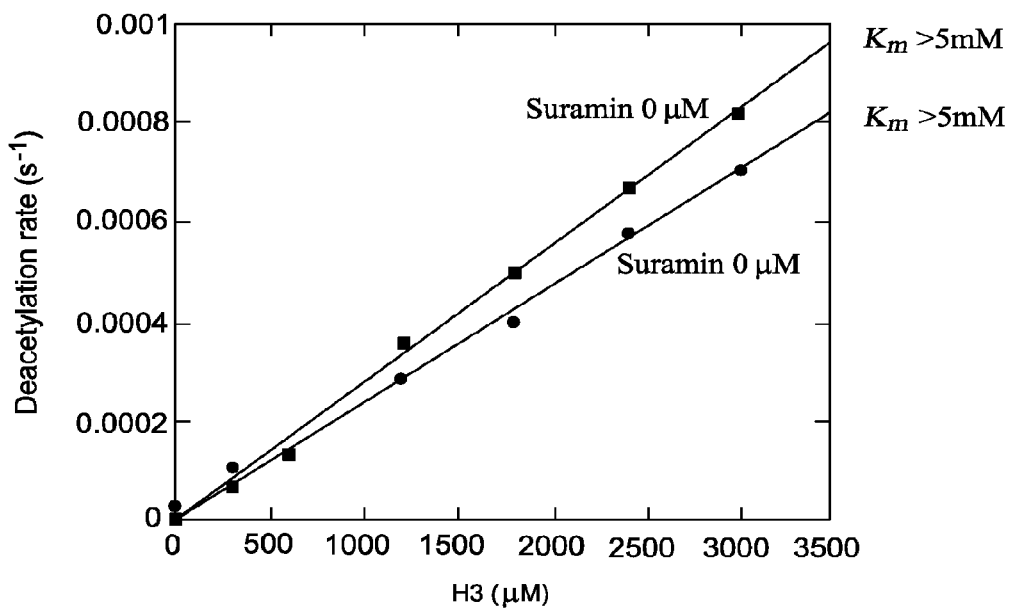
Figure 17B:
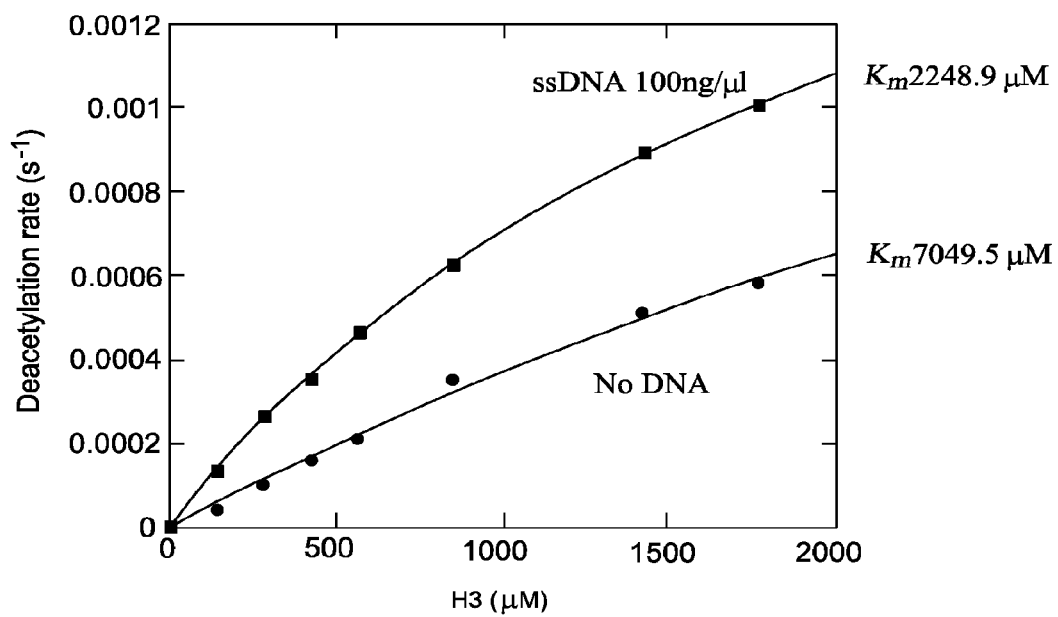

FIG. 17 illustrates $K_m$ of H3, $K_m$ of NAD of SirT6Δ2-18 in the presence of suramin or ssDNA.

DETAILED DESCRIPTION OF THE INVENTION

The invention provides a method of increasing a deacetylase activity of SIRT6, wherein the method comprises contacting the enzyme with an agent that binds SIRT6 and reduces the $K_m$ of SIRT6 for a substrate, thereby increasing the deacetylase activity of SIRT6.

Compounds that increase the deacetylase activity of SIRT6 are referred to herein as "activating compounds." In certain embodiments, the method may comprise contacting SIRT6 with an activating compound having a structure represented by formula (I) as described herein.

SIRT6 may be activated in vitro, e.g., in a solution or in a cell. In one embodiment, SIRT6 is contacted with an activating compound in a solution. SIRT6 is activated by a compound when at least one of its biological activities, e.g., deacetylation activity, is higher in the presence of the compound than in its absence. Activation may be by a factor of at least about 10%, 30%, 50%, 100% (i.e., a factor of two), 3, 10, 30, or 100. The extent of activation can be determined, e.g., by contacting the activated SIRT6 with a deacetylation substrate and determining the extent of deacetylation of the substrate, as further described herein. The observation of a lower level of acetylation of the substrate in the presence of a test SIRT6 relative to the presence of a non-activated control SIRT6 indicates that the test SIRT6 is activated. The solution may be a reaction mixture. The solution may be in a dish, e.g., a multiwell dish. SIRT6 may be prepared recombinantly or isolated from cells according to methods known in the art.

In another embodiment, a cell comprising SIRT6 is contacted with an activating compound. The cell may be a eukaryotic cell, e.g., a mammalian cell, such as a human cell, a yeast cell, a non-human primate cell, a bovine cell, an ovine cell, an equine cell, a porcine cell, a sheep cell, a bird (e.g., chicken or fowl) cell, a canine cell, a feline cell or a rodent (mouse or rat) cell. It can also be a non-mammalian cell, e.g., a fish cell. Yeast cells include *S. cerevesiae* and *C. albicans*. The cell may also be a prokaryotic cell, e.g., a bacterial cell. The cell may also be a single-cell microorganism, e.g., a protozoan. The cell may also be a metazoan cell, a plant cell or an insect cell. Preferably, the cell is a eukaryotic cell In one embodiment, the cells are in vitro. A cell may be contacted with a solution having a concentration of an activating compound of less than about 0.1 µM, 0.5 µM, less than about 1 µM, less than about 10 µM, less than about 100 µM, less than about 250 µM, less than about 500 µM, or less than about 1000 µM. The concentration of the activating compound may also be in the range of about 0.1 to 1 µM, about 1 to 10 µM, about 10 to 100 µM, 10 to 250 µM, 10 to 500 µM, or 10 to 1000 µM. The appropriate concentration may depend on the particular compound and the particular cell used as well as the desired effect. For example, a cell may be contacted with a "SIRT6 activating" concentration of an activating compound, e.g., a concentration sufficient for activating the SIRT6 by a factor of at least 10%, 30%, 50%, 100%, 3, 10, 30, or 100.

In certain embodiments, a cell is contacted with an activating compound in vivo, such as in a subject. The subject can be a human, a non-human primate, a bovine, an ovine, an equine, a porcine, a sheep, a canine, a feline or a rodent (mouse or rat). For example, an activating compound may be administered to a subject. Administration may be local, e.g., topical, parenteral, oral, or other depending on the desired result of the administration (as further described herein). Administration may be followed by measuring a factor in the subject or the cell, such as the activity of the SIRT6 or a clinical marker of a urea cycle disorder such as levels of ammonia, ornithine, uracil, orotic acid, citrulline, arginosuccinic acid, and/or arginine. In an illustrative embodiment, a cell is obtained from a subject following administration of an activating compound to the subject, such as by obtaining a biopsy, and the activity of the SIRT6 is determined in the biopsy. The cell may be any cell of the subject, but in cases in which an activating compound is administered locally, the cell is preferably a cell that is located in the vicinity of the site of administration.

In one embodiment, a screening assay comprises (i) contacting a SIRT6 with a test agent and an acetylated substrate under conditions appropriate for the SIRT5 to deacetylate the substrate in the absence of the test agent, and (ii) determining the level of acetylation of the substrate, wherein a lower level of acetylation of the substrate in the presence of the test agent relative to the absence of the test agent indicates that the test agent stimulates deacetylation by the SIRT6, whereas a higher level of acetylation of the substrate in the presence of the test agent relative to the absence of the test agent indicates that the test agent inhibits deacetylation by the SIRT6.

Methods for identifying an agent that modulates, e.g., stimulates or inhibits, SIRT6 in vivo may comprise (i) contacting a cell with a test agent and a substrate that is capable of entering a cell under conditions appropriate for the SIRT6 to deacetylate the substrate in the absence of the test agent, and (ii) determining the level of acetylation of the substrate, wherein a lower level of acetylation of the substrate in the presence of the test agent relative to the absence of the test agent indicates that the test agent stimulates deacetylation by SIRT6, whereas a higher level of acetylation of the substrate in the presence of the test agent relative to the absence of the test agent indicates that the test agent inhibits deacetylation by SIRT6. The method may further comprise lysing the cells to determine the level of acetylation of the substrate. Substrates may be added to cells at a concentration ranging from about 0.001 to about 1 mM, preferably from about 0.01 mM to about 1 mM, and more preferably from about 0.1 mM to about 1 mM.

The acetylated substrate can be any suitable substrate that undergoes deacetylation by the action of SIRT6. The acetylated substrate can be an endogenous substrate. Non-limiting examples of other suitable substrates include p300, acetylated H3, unmodified H3, and acetylated H4. The sequences of the aforesaid substrates can be as described herein.

In some embodiments, whether in vitro or in vivo, a cell may also be contacted with more than one agent. Preferably, at least one agent comprises an activating compound as described herein. Additional agent(s) may comprise at least one activating compound but can comprise at least one inhibiting compound, e.g., an agent that inhibits the deacetylase activity of SIRT6. In such embodiments, the activity of SIRT6 can be modulated by the differing actions of the activating compound and the inhibiting compound.

The level of acetylation of the substrate can be determined using any suitable assay method. In an embodiment, HPLC can be utilized to separate and quantitate the levels of an acetylated and a deacetylated substrate.

In certain embodiments, the method comprises contacting SIRT6 with an agent, wherein the agent is a compound of the formula (I):

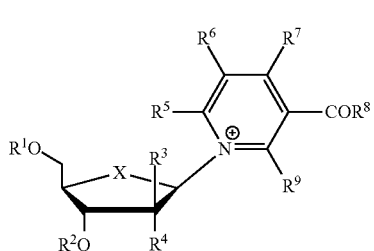

wherein $R^1$ is hydrogen or $PO_3H_2$,
$R^3$ and $R^4$ are independently selected from the group consisting of hydrogen, F, Cl, Br, and I,
$R^2$ is hydrogen or a group of the formula:

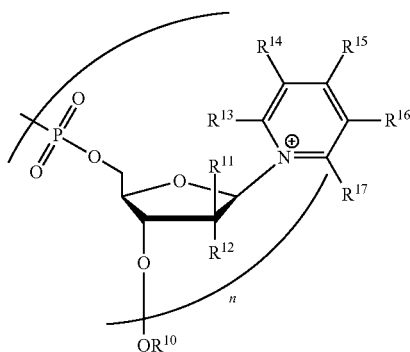

wherein $R^{10}$ is hydrogen or $PO_3H_2$,
$R^{11}$ and $R^{12}$ are independently selected from the group consisting of hydrogen, F, Cl, Br, and I,
$R^8$ is amino or $C_1$-$C_6$ alkyl,
each of $R^5$, $R^6$, $R^7$, $R^9$, $R^{13}$, $R^{14}$, $R^{15}$, and $R^{17}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together or $R^6$ and $R^7$ taken together form a 5- or 6-membered saturated or unsaturated ring, and n is 0 to 28.

For the compound of the formula (I), in certain embodiments, $R^2$ is hydrogen. In certain embodiments, n is 1. In certain embodiments, $R^8$ is amino. In certain embodiments, $R^5$, $R^6$, $R^7$, and $R^9$ are hydrogen. In preferred embodiments, $R^3$ and $R^4$ are fluoro. In preferred embodiments, $R^3$ and $R^4$ are chloro. In preferred embodiments, $R^3$ is hydrogen and $R^4$ is fluoro.

In preferred embodiments, the compound of the formula (I) is selected from the group consisting of 1-(2-deoxy-2-fluoro-D-ribofuranosyl)-nicotinamide, 1-(2'-deoxy-2',2'-difluoro-ribofuranosyl)-nicotinamide, and 2'-deoxy-2'-fluoro-ribo-nicotinamide mononucleotide.

In certain embodiments, the method comprises contacting SIRT6 with an agent,
wherein the agent is a compound of the formula (II):

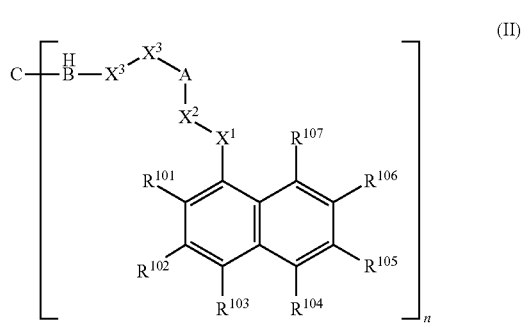

wherein $X^1$ and $X^2$ are independently selected from the group consisting of —O—, —C(=))—, —N($R^{108}$)—, —C($R^{109}$)$_2$—, —C(=S)—, —S—, —S(=O)—, and —S(=O)$_2$— and $X^3$ and $X^4$ are absent or are independently selected from the group consisting of —O—, —C(=))—, —N($R^{108}$)—, —C($R^{109}$)$_2$—, —C(=S)—, —S—, —S(=O)—, and —S(=O)$_2$—, A is selected from the group consisting of alkylene, cycloalkylene, heterocycloalkylene, arylene, or heteroarylene optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfamoyl, sulfonyl, sulfoxido, and phosphate, B is selected from the group consisting of a bond, alkyl, cycloalkyl, heterocycloalkyl, aryl, or heteroaryl optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfonyl, sulfoxido, and phosphate, C is absent or is selected from the group consisting of —NHC(=O)NH—, —C(=O)—, alkylene, and arylene, $R^{101}$, $R^{102}$, $R^{103}$, $R^{104}$, $R^{105}$, $R^{106}$, and $R^{107}$ are independently hydrogen, alkyl, cycloalkyl, heterocycloalkyl, aryl, or heteroaryl optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfonyl, sulfoxido, or phosphate, $R^{108}$ and $R^{109}$ are independently selected from the group consisting of hydrogen and $C_1$-$C_6$ alkyl, when C is absent, n is 1 and when C is —NHC(=O)NH—, —C(=O)—, alkylene, or arylene, n is 2.

For the compound of the formula (II), in certain embodiments, C is absent, and n is 1. In certain embodiments, each of $X^1$ and $X^3$ is —NH—, and each of $X^2$ and $X^4$ is —C(=O)—. In a preferred embodiment, A is 1,3-phenylene or 1,4-phenylene. In a preferred embodiment, B is phenyl, more preferably 3-aminophenyl or 4-aminophenyl. In a preferred embodiment, $R^{103}$, $R^{105}$, and $R^{107}$ are independently sulfate or phosphate.

In a preferred embodiment, the compound has the formula (IIa) or (IIb):

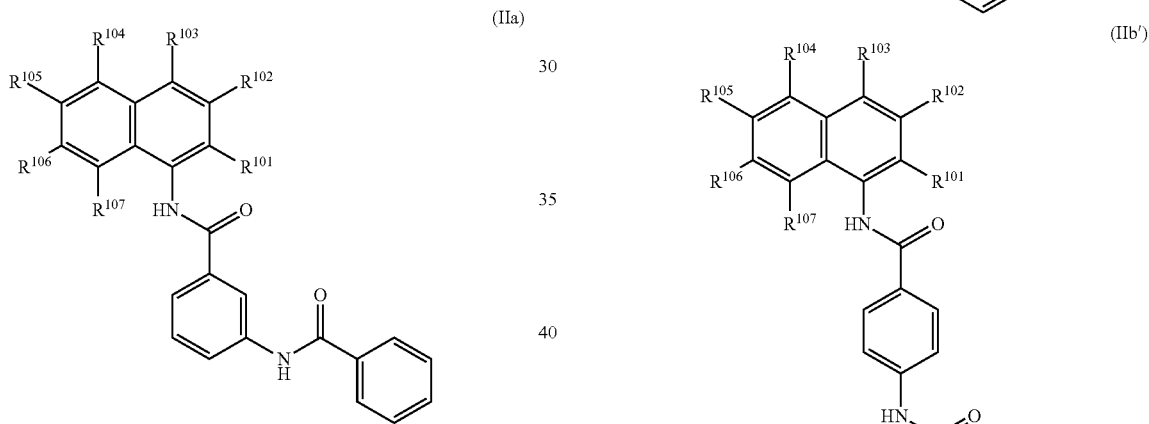

(IIa)

(IIb)

wherein any open position can be optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfamoyl, sulfonyl, sulfoxido, and phosphate.

In another preferred embodiment, the compound has the formula (IIa') or (IIb'):

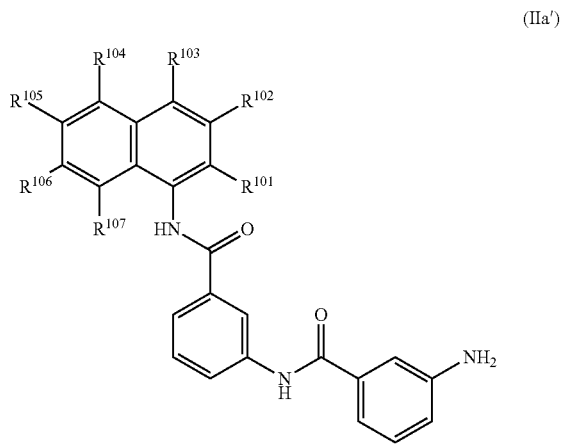

(IIa')

(IIb')

wherein $R^{103}$, $R^{105}$, and $R^{107}$ are independently selected from the group consisting of hydrogen, sulfate, and phosphate, with the proviso that each of $R^{103}$, $R^{1105}$, and $R^{107}$ are not all hydrogen, wherein all other provisos also apply.

For the compound of the formula (IIa), (IIb), (IIa'), or (IIb'), in certain embodiments, C is —C(=O)—, and n is 2. In certain embodiments, each of $X^1$ and $X^3$ is —NH—, and each of $X^2$ and $X^4$ is —C(=O)—. In a preferred embodiment, A is 1,3-phenylene or 1,4-phenylene. In a preferred embodiment, B is phenyl, more preferably 3-aminophenyl or 4-aminophenyl.

In a preferred embodiment, the compound has the formula (IIc) or (IId):

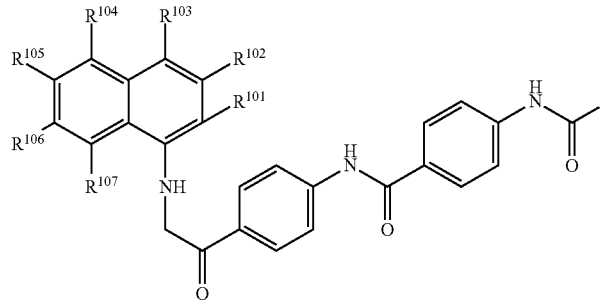
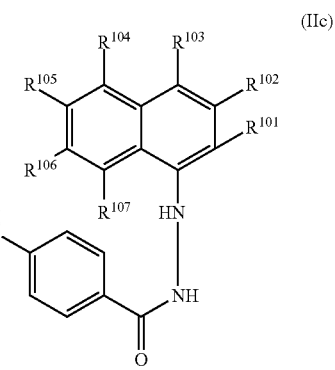

(IIc)

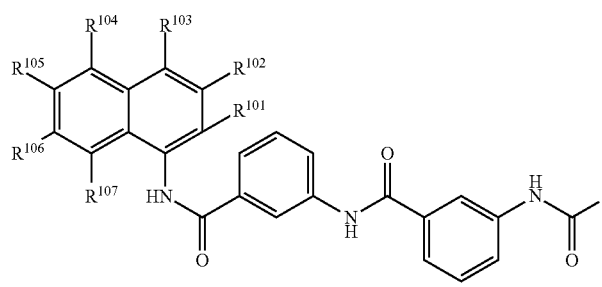
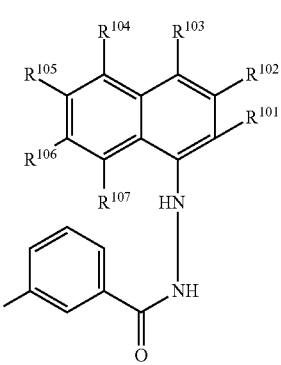

(IId)

wherein any open position can be optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfamoyl, sulfonyl, sulfoxido, and phosphate. In a preferred embodiment, $R^{103}$, $R^{105}$, and $R^{107}$ are independently selected from the group consisting of hydrogen, sulfate, and phosphate, with the proviso that each of $R^{103}$, $R^{105}$, and $R^{107}$ are not all hydrogen, wherein all other provisos also apply.

For the compound of the formula (IIc) or (IId), in a first set of certain embodiments, C is —NHC(=O)NH—, and n is 2. In certain embodiments, each of $X^1$ and $X^3$ is —NH—, and each of $X^2$ and $X^4$ is —C(=O)—. In preferred embodiments, A is 1,3-phenylene or 1,4-phenylene. In certain embodiments, B is 1,3-phenylene or 1,4-phenylene. In certain embodiments, B is a bond, $X^1$ is NH, $X^2$ is —C(=O)—, and $X^3$ and $X^4$ are absent.

For the compound of the formula (IIc) or (IId), in a second set of certain embodiments, C is alkylene or arylene, and n is 2. In certain embodiments, each of $X^1$ and $X^3$ is —NH—, and each of $X^2$ and $X^4$ is —C(=O)—. In preferred embodiments, A is 1,3-phenylene or 1,4-phenylene. In preferred embodiments, B is phenyl, more preferably 3-aminophenyl or 4-aminophenyl. In certain of the above embodiments, $R^{103}$, $R^{105}$, and $R^{107}$ are independently sulfate or phosphate.

In a preferred embodiment, the compound has the formula (IIe):

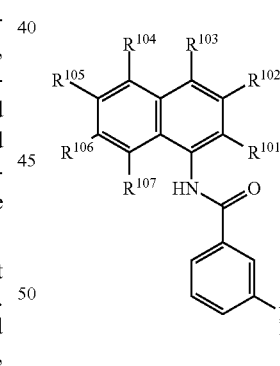
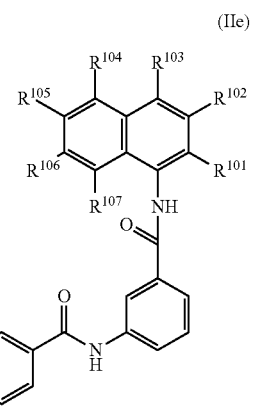

(IIe)

wherein any open position can be optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfamoyl, sulfonyl, sulfoxido, and phosphate. In a preferred embodiment, $R^{103}$, $R^{105}$, and $R^{107}$ are independently selected from the group consisting of hydrogen, sulfate, and phosphate, with the proviso that each of $R^{103}$, $R^{105}$, and $R^{107}$ are not all hydrogen, wherein all other provisos also apply.

In a preferred embodiment, the compound has the formula (IIf):

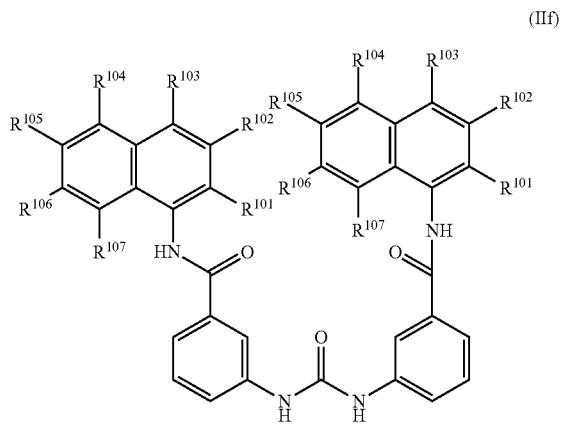

(IIf)

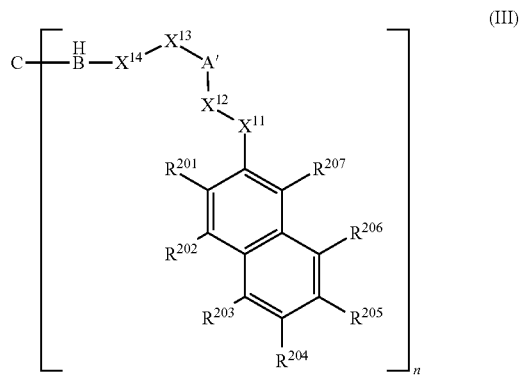

(III)

wherein any open position can be optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfamoyl, sulfonyl, sulfoxido, and phosphate. In a preferred embodiment, $R^{103}$, $R^{105}$, and $R^{107}$ are independently selected from the group consisting of hydrogen, sulfate, and phosphate, with the proviso that each of $R^{103}$, $R^{105}$, and $R^{107}$ are not all hydrogen, wherein all other provisos also apply.

In a preferred embodiment, the compound has the formula (IIg):

wherein $X^{11}$, $X^{12}$, $X^{13}$, and $X^{14}$ are independently selected from the group consisting of —O—, —C(=))—, —N($R^{208}$)—, —C($R^{209}$)$_2$—, —C(=S)—, —S—, —S(=O)—, and —S(=O)$_2$—, A is selected from the group consisting of alkylene, cycloalkylene, heterocycloalkylene, arylene, or heteroarylene optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfamoyl, sulfonyl, sulfoxido, and phosphate, B is selected from the group consisting of a bond, alkyl, cycloalkyl, heterocycloalkyl, aryl, or heteroaryl optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfonyl, sulfoxido, and phosphate,

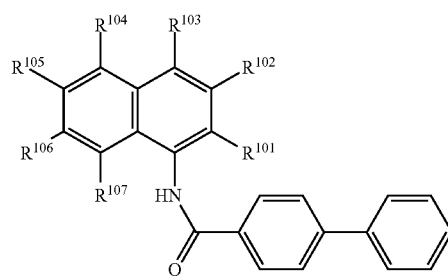

(IIg)

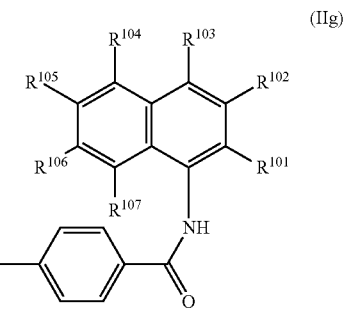

wherein any open position can be optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfamoyl, sulfonyl, sulfoxido, and phosphate. In a preferred embodiment, $R^{103}$, $R^{105}$, and $R^{107}$ are independently selected from the group consisting of hydrogen, sulfate, and phosphate, with the proviso that each of $R^{103}$, $R^{105}$, and $R^{107}$ are not all hydrogen, wherein all other provisos also apply.

In certain embodiments, the method comprises contacting SIRT6 with an agent, wherein the agent is a compound of the formula (III):

C is absent or is selected from the group consisting of —NHC(=O)NH—, —C(=O)—, alkylene, and arylene, $R^{201}$, $R^{202}$, $R^{203}$, $R^{204}$, $R^{205}$, $R^{206}$, and $R^{207}$ are independently hydrogen, alkyl, cycloalkyl, heterocycloalkyl, aryl, or heteroaryl optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfonyl, sulfoxido, or phosphate, $R^{208}$ and $R^{209}$ are hydrogen or $C_1$-$C_6$ alkyl, when C is absent, n is 1 and when C is —C(=O)—, —NHC(=O)NH—, alkylene, or arylene, n is 2.

For the compound of the formula (III), in a first set of certain embodiments, C is absent, and n is 1. In certain embodiments, each of $X^{11}$ and $X^{13}$ is —NH—, and each of $X^{12}$ and $X^{14}$ is —C(=O)—. In a preferred embodiment, A is 1,3-phenylene or 1,4-phenylene. In a preferred embodiment, B is phenyl, more preferably 3-aminophenyl or 4-aminophenyl. In a preferred embodiment, $R^{203}$, $R^{205}$, and $R^{207}$ are independently sulfate or phosphate.

For the compound of the formula (III), in a second set of embodiments, C is —C(=O)—, and n is 2. In certain embodiments, each of $X^{11}$ and $X^{13}$ is —NH—, and each of $X^{12}$ and $X^{14}$ is —C(=O)—. In a preferred embodiment, A is 1,3-phenylene or 1,4-phenylene. In a preferred embodiment, B is phenyl, more preferably 3-aminophenyl or 4-aminophenyl.

For the compound of the formula (III), in a third set of embodiments, C is —NHC(=O)NH—, and n is 2. In certain embodiments, each of $X^{11}$ and $X^{13}$ is absent or —NH—, and each of $X^{12}$ and $X^{14}$ is absent or —C(=O)—. In preferred embodiments, A is 1,3-phenylene or 1,4-phenylene. In certain embodiments, B is a bond, 1,3-phenylene, or 1,4-phenylene. For example, in certain embodiments, B is a bond, $X^{11}$ is —NH—, $X^{12}$ is —C(=O)—, and $X^{13}$ and $X^{14}$ are absent.

For the compound of the formula (III), in a fourth set of embodiments, C is alkylene or arylene, and n is 2. In certain embodiments, each of $X^{11}$ and $X^{13}$ is —NH—, and each of $X^{12}$ and $X^{14}$ is —C(=O)—. In preferred embodiments, A is 1,3-phenylene or 1,4-phenylene. In preferred embodiments, B is phenyl, more preferably, 3-aminophenyl or 4-aminophenyl. In certain of the above embodiments, $R^{203}$, $R^{205}$, and $R^{207}$ are independently sulfate or phosphate.

In a preferred embodiment, the compound has the formula (IIIa);

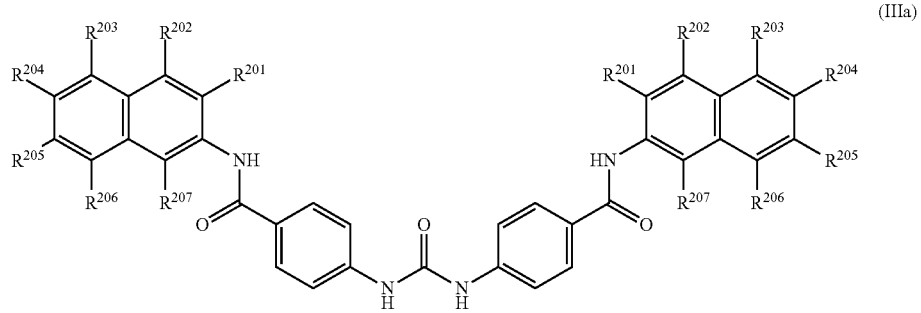

(IIIa)

wherein any open position can be optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, amino, carboxyl, carbamoyl, alkoxy, sulfonate, sulfate, sulfonylamido, sulfamoyl, sulfonyl, sulfoxido, and phosphate. In a preferred embodiment, $R^{103}$, $R^{105}$, and $R^{107}$ are independently selected from the group consisting of hydrogen, sulfate, and phosphate, with the proviso that each of $R^{202}$, $R^{204}$, and $R^{206}$ are not all hydrogen, wherein all other provisos also apply.

DEFINITIONS

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "alkylene," as used herein, means a straight-chain or branched alkyl substituent containing from, for example, 1 to about 6 carbon atoms, preferably from 1 to about 4 carbon atoms, and is connected to two or more substituents at two or more different positions on the alkylene group.

The term "alkenyl," as used herein, means a linear alkenyl substituent containing at least one carbon-carbon double bond and from, for example, about 2 to about 6 carbon atoms (branched alkenyls are about 3 to about 6 carbons atoms), preferably from about 2 to about 5 carbon atoms (branched alkenyls are preferably from about 3 to about 5 carbon atoms), more preferably from about 3 to about 4 carbon atoms. Examples of such substituents include vinyl, propenyl, isopropenyl, n-butenyl, sec-butenyl, isobutenyl, tert-butenyl, pentenyl, isopentenyl, hexenyl, and the like.

The term "alkenylene," as used herein, means a straight-chain or branched alkenyl substituent containing from, for example, 2 to about 6 carbon atoms, preferably from 2 to about 4 carbon atoms, and is connected to two or more substituents at two or more different positions on the alkenylene group.

The term "alkynyl," as used herein, means a linear alkynyl substituent containing at least one carbon-carbon triple bond and from, for example, 2 to about 6 carbon atoms (branched alkynyls are about 3 to about 6 carbons atoms), preferably from 2 to about 5 carbon atoms (branched alkynyls are preferably from about 3 to about 5 carbon atoms), more preferably from about 3 to about 4 carbon atoms. Examples of such substituents include ethynyl, propynyl, isopropynyl, n-butynyl, sec-butynyl, isobutynyl, tert-butynyl, pentynyl, isopentynyl, hexynyl, and the like.

The term "alkynylene," as used herein, means a straight-chain or branched alkynyl substituent containing from, for example, 2 to about 6 carbon atoms, preferably from 2 to about 4 carbon atoms, and is connected to two or more substituents at two or more different positions on the alkynylene group.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The term "cycloalkenyl," as used herein, means the same as the term "cycloalkyl," however one or more double bonds are present. Examples of such substituents include cyclopentenyl and cyclohexenyl. The cyclic alkyl groups may be unsubstituted or further substituted with alkyl groups such as methyl groups, ethyl groups, and the like.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable bicyclic heterocyclyl groups include monocylic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. Preferably, the heterocyclyl group is an aromatic heterocyclyl group. Non-limiting examples of suitable heterocyclyl groups include furanyl, thiopheneyl, pyrrolyl, pyrazolyl, imidazolyl, 1,2,3-triazolyl, 1,2,4-triazolyl, isoxazolyl, oxazolyl, isothiazolyl, thiazolyl, pyridinyl, pyrimidinyl, pyrazinyl, triazinyl, benzofuranyl, benzothiopheneyl, indolyl, quinolinyl, isoquinolinyl, benzimidazolyl, benzoxazolinyl, benzothiazolinyl, and quinazolinyl. The heterocyclyl group is optionally substituted with 1, 2, 3, 4, or 5 substituents as recited herein, wherein the optional substituent can be present at any open position on the heterocyclyl group.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise $4n+2\pi$ electrons, according to Hückel's Rule.

The term "arylene" refers to an unsubstituted or substituted aromatic carbocyclic substituent as defined herein, wherein the arylene substituent is connected to two or more substituents at two or more different positions on the arylene group. For example, 1,2-dichlorobenzene can be considered to be a phenylene (arylene) group substituted with two chlorine atoms.

The term "arylalkyl," as used herein, refers to aryl group having an alkyl group attached thereto. The arylalkyl group can be substituted at any position of the aryl group or the alkyl group. The term "cycloalkylalkyl," as used herein, refers to cycloalkyl group having an alkyl group attached thereto. The cycloalkylalkyl group can be substituted at any position of the cycloalkyl group or the alkyl group.

Whenever a range of the number of atoms in a structure is indicated (e.g., a $C_1$-$C_{12}$, $C_1$-$C_8$, $C_1$-$C_6$, $C_1$-$C_4$, or $C_2$-$C_{12}$, $C_2$-$C_8$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (e.g., $C_6$-$C_{10}$) as used with respect to any chemical group (e.g., aryl) referenced herein encompasses and specifically describes 6, 7, 8, 9, and/or 10 carbon atoms, as appropriate, as well as any sub-range thereof (e.g., 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

Salts

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a quinoline group or a dimethylaminoalkyl group) include hydrochloride and hydrobromide salts. The compounds of the invention containing an acidic or basic moiety are useful in the form of the free base or acid or in the form of a pharmaceutically acceptable salt thereof.

It should be recognized that the particular counter ion forming a part of any salt of this invention is usually not of a critical nature, so long as the salt as a whole is pharmacologically acceptable and as long as the counter ion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

Formulations

The invention is further directed to a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the invention chosen, as well as by the particular method used to administer the composition. Accordingly, there is a wide variety of suitable formulations of the pharmaceutical composition of the invention. The following formulations for oral, aerosol, nasal, pulmonary, parenteral, subcutaneous, intravenous, intra-arterial, intramuscular, intraperitoneal, intrathecal, intratumoral, topical, rectal, and vaginal administration are merely exemplary and are in no way limiting.

The pharmaceutical composition can be administered parenterally, e.g., intravenously, intraarterially, subcutaneously, intradermally, or intramuscularly. Thus, the invention provides compositions for parenteral administration that comprise a solution or suspension of the inventive compound or salt dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice*, J.B. Lippincott Company, Philadelphia, pp. 238-250 (1982), and Toissel, *ASHP Handbook on Injectable Drugs*, 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the invention may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound or salt of the invention, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the invention may be made into suppositories by mixing with a variety of bases, such as emulsifying bases or water-soluble bases. Formulations suitable for vaginal administration may be presented as vaginal rings (i.e., intravaginal rings), pessaries, tampons, creams, gels, pastes, foams, or spray formulas containing, in addition to the active ingredient, such carriers as are known in the art to be appropriate.

It will be appreciated by one of ordinary skill in the art that, in addition to the afore described pharmaceutical compositions, the compound or salt of the invention may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, for example hepatic cells, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9: 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the invention may be administered intravenously, locally, topically, etc. in a dose that varies according to the mode of administration, the agent being delivered, and the stage of disease being treated.

The invention further provides a compound of the formula (II):

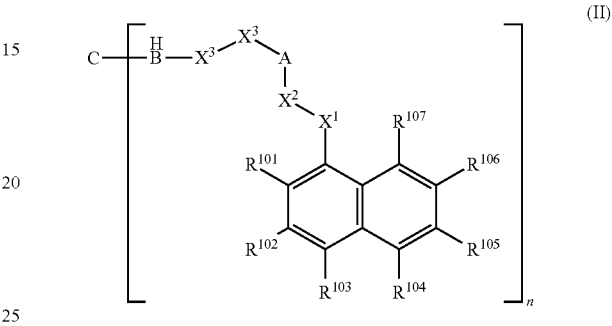

with the provisos that:
when C is arylene, $R^{103}$, $R^{105}$, and $R^{107}$ are not all sulfate;
when C is arylene substituted with alkyl, $R^{103}$ and $R^{105}$ are not both sulfate, and $R^{103}$ and $R^{107}$ are not both sulfate;
when B is a bond and C is —NHC(=O)NH—, $R^{103}$, $R^{105}$, and $R^{107}$ are not all sulfate, $R^{103}$ and $R^{105}$ are not both sulfate, and $R^{103}$ and $R^{107}$ are not both sulfate;
when A is 1,4-biphenylene, $R^{103}$, $R^{105}$, and $R^{107}$ are not all sulfate;
when A is 1,3-phenylene substituted with alkyl, alkoxy, halo, or carboxy, and B is amino-substituted phenyl, $R^{103}$, $R^{105}$, and $R^{107}$ are not all sulfate,
when A is 1,3-phenylene and B is amino-substituted phenyl, $R^{105}$ and $R^{107}$ are not both sulfate, and $R102$ and $R^{107}$ are not both sulfate;
when A is 1,4-phenylene and B is amino-substituted phenyl, $R^{105}$ and $R^{107}$ are not both sulfate, and $R^{102}$ and $R^{107}$ are not both sulfate; and
when A and B are both 1,3-phenylene, $R^{103}$, $R^{105}$, and $R^{107}$ are not all sulfate.

The compound of formula (II) can be as described herein in connection with the method embodiment of the invention.

The invention additionally provides a compound of the formula (III):

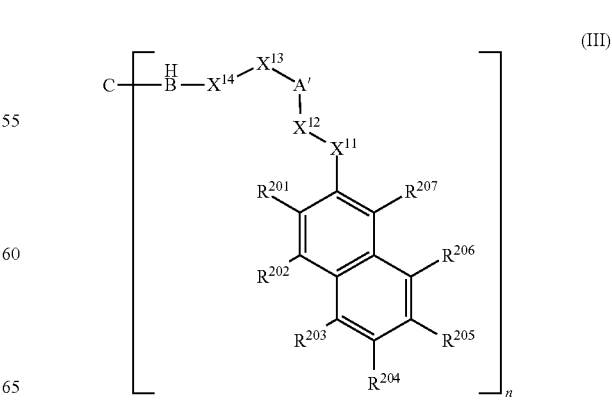

with the proviso that, when C is arylene, $R^{202}$ and $R^{206}$ are not both sulfate.

The compound of formula (III) can be as described herein in connection with the method embodiment of the invention.

The following examples further illustrate the invention but, of course, should not be construed as in any way limiting its scope.

The peptides acetylated H3 ARTKQTAR(K-Ac)STGG(K-Ac)APRKQLAS (SEQ ID NO: 1), unmodified H3 ARTKQTARKSTGGKAPRKQLAS (SEQ ID NO: 2), and acetylated H4 SGRG(K-Ac)GG(K-Ac)GLG(K-Ac)GGA(K-Ac)RHR (SEQ ID NO: 3) were synthesized by the Proteomics Resource Center at Rockefeller University. They were purified by HPLC before use. All other chemicals were purchased from Sigma-Aldrich or VWR. HPLC was performed on a Hitachi Elite LaChrom system using C18 reverse phase columns.

Plasmid Construction and Protein Expression

The gene encoding human SIRT6 was amplified by PCR reaction. The PCR product was then cloned into pSTblue-1 (Novagen). After digestion with NheI and BamHI, the fragment containing SIRT6 gene was ligated into pET28a vector (Novagen), which rendered SIRT6 an N-terminal poly-histidine tag. The SIRT6 sequence in pET28a plasmid was confirmed by DNA sequencing. The pET28a-SIRT6 was then transformed into BL21Codon-plus RIPL cells (Stratagene) and the protein expression was induced by adding 500 µM IPTG after the cells grew to the density of about 0.7. After 1 hour induction at 37° C., the cells were pelleted and lysed by freeze-thaw cycles. The protein was purified by Ni-NTA affinity resin and eluted by phosphate buffer containing 200 mM imidazole. The protein was then loaded onto a DEAE column which had been equilibrated with 10 mM phosphate, 50 mM NaCl, pH 7.2. The protein was eluted by 4.5 ml of the same buffer followed by 1.5 ml of 10 mM phosphate, 600 mM NaCl, pH7.2. The fractions were pooled and concentrated using Centricon Plus-20 (Millipore). After adding 15% glycerol and 2.5 mM DTT, the proteins were then aliquatted and stored at −80° C.

The truncated SIRT6 was cloned similarly with the full length SIRT6. The primers used in the cloning of different truncated SIRT6 are the following: SIRT6Δ2-7 Forward 5' GCTAGC ATG GGG CTG TCG CCG TAC GCG 3' (SEQ ID NO: 4); SIRT6Δ2-12 Forward 5' GCTAGC ATG GCGGA-CAAGGGCAAGTGCGGC 3' (SEQ ID NO: 5); SIRT6Δ2-18 Forward 5' GCTAGC ATG GGC CTC CCG GAG ATC TTC GAC 3' (SEQ ID NO: 6); SIRT6Δ2-51 Forward 5' 5' GCTAGC ATG ACG GGT GCC GGC ATC AGC ACT 3' (SEQ ID NO: 7). The common reverse primer is 5'GGATC-CCCAAGCACCCTGGTCAGCTG 3' (SEQ ID NO: 8). The truncated SIRT6 was amplified by PCR reaction. The PCR product was then ligated into pSTblue-1 (Novagen). After digestion with NheI and BamHI, the fragment containing SIRT6 gene was ligated into pET28a vector (Novagen). The SIRT6 truncated sequence in pET28a plasmid was confirmed by DNA sequencing, and the plasmid was then transformed into BL21Codon-plus RIPL cells (Stratagene). The protein expression and purification were the same as the full length SIRT6 as described above.

EXAMPLE 1

This example demonstrates the determination of $K_d$ of suramin by HPLC.

Deacetylation reactions catalyzed by SIRT6 were carried out in 100 mM phosphate buffer pH 7.5, containing 800 µM NAD, 12 µM SirT6, 300 µM H3 and different concentrations of suramin. The reactions were incubated at 37° C. for 2 hours and then quenched by adding 4 µl of 10% trifluoroacetic acid. The precipitated proteins and other insolubles were removed by centrifugation at 15,000 rpm for 5 minutes. The peptides were separated by a Waters Xterra RP-18 column using a gradient of 0-30% acetonitrile in 0.1% trifluoroacetic acid. The peptide and the deacetylated peptide were quantified by integrating their area in the chromatography at the wavelength of 215 nm. The turnover rates versus peptide concentration were plotted and fitted to the equation: Activation (Fold)=1+m*x/($K_d$+x) using the software Kaleidagraph.

EXAMPLE 2

This example demonstrates the determination of $K_d$ of DNA by HPLC.

In the enzymatic reaction, the following DNA was used.

Calf thymus DNA (USB Corporation), which was digested with EcoRI and then purified using Spinprep Gel DNA Kit (Novagen);

ssDNA (5' GGGGATCCATGAAGATGAGCTTTGCGT-TGACT 3' (SEQ ID NO: 9), Integrated DNA Technologies);

dsDNA (forward 5' AAGCATTTATCAGGGTTAT-TGTCTCATGAGCGGAT 3' (SEQ ID NO: 10), reverse 5' ATCCGCTCATGAGACAATAACCCTGATAAATGCTT 3' (SEQ ID NO: 11), Integrated DNA Technologies); and pSTBlue plasmid, which was amplified using DH5α cells and purified by WIZARD™ PLUS (Midiprep) DNA purification system (Promega).

Deacetylation reactions were carried out in 100 mM phosphate buffer pH7.5, containing 800 µM NAD, 10 µM SIRT6, 480 µM H3 and DNA with different concentrations. The reactions were incubated at 37° C. for 2 hours and then quenched by adding 5.6 µl of 10% trifluoroacetic acid in 35 µl reaction. The precipitated proteins and other insolubles were removed by centrifugation at 15,000 rpm for 5 minutes. DNA in the supernatant was further removed by centrifugation at 15,000 rpm for 10 minutes using Microcon with 10 kDa cutoff (Millipore). In the experiment with the digested calf thymus DNA, the peptides were separated by a Waters Xterra RP-18 column using a gradient of 0-30% acetonitrile in 0.1% trifluoroacetic acid. The peptide and the deacetylated peptide were quantified by integrating their area in the chromatography at the wavelength of 215 nm. The samples from the reaction involving ssDNA, dsDNA, and pSTBlue was separated by a C18 reverse column (EC250/4.6 NUCLEOSIL 100-5 C18, Macherey-Nagel) using 20 mM ammonia acetate as eluent. AADPR were quantified by integrating their area in the chromatography at the wavelength of 260 nm. The turnover rates versus DNA concentration were plotted and fit to the equation: Activation (Fold)=1+m*x/($K_d$+x) using the software Kaleidagraph.

EXAMPLE 3

This example demonstrates the determination of $K_m$ of H3 of SIRT6 and truncated forms by HPLC.

The SIRT6 enzymatic reactions were carried out in 100 mM phosphate buffer pH7.5, containing 800 µM NAD, 10 µM SirT6/truncated forms, and H3 with different concentrations. The reactions were incubated at 37° C. for 2 hours. To test the activation effect of suramin and DNA, 50 µM of suramin or 100 ng/µl ssDNA was used. After quenching with 10% trifluoroacetic acid, the precipitates in the reactions were removed by centrifugation. DNA in the supernatant was further removed using Microcon with 10 kDa cutoff (Millipore). AADPR was separated from other components in the reaction by a C18 reverse column (EC250/4.6 NUCLEOSIL 100-5 C18, Macherey-Nagel) using 20 mM ammonium acetate as the eluent, and then quantified by integrating their area in the chromatography at the wavelength of 260 nm. The turnover rates versus the peptide concentration were plotted and fit to the Michaelis-Menten equation using the software Kaleidagraph.

EXAMPLE 4

This example demonstrates the determination of $K_m$ of NAD of SIRT6 and truncated forms by HPLC.

The SIRT6 enzymatic reactions were carried out in 100 mM phosphate buffer pH7.5, containing 1 mM H3, and 10 µM SIRT6/truncated forms. The NAD concentration in the reactions was changed as indicated. To test the activation effect of suramin and DNA on $K_m$ of NAD, 50 µM of suramin or 100 ng/µl ssDNA was used. After 2 hours incubation at 37° C., the reactions were quenched with 10% trifluoroacetic acid and the precipitates were removed by centrifiguation at 15,000 rpm for 10 minutes. The reactions involving DNA were further centrifuged in Microcon with 10 kDa cutoff (Millipore) to remove DNA and proteins. AADPR was separated from other components in the reaction by a C18 reverse column (EC250/4.6 NUCLEOSIL 100-5 C18, Macherey-Nagel) using 20 mM ammonium acetate as the eluent, and then quantified by integrating their area in the chromatography at the wavelength of 260 nm. The turnover rates versus the peptide concentration were plotted and fitted to the Michaelis-Menten equation using the software Kaleidagraph.

EXAMPLE 5

This example describes a particular gel shift assay.

The plasmid pSTBlue was linearized by EcoRI, BamHI, or EcoRV, and then purified by DNA gel extraction kit (Novagen) or GENECLEAN™ III kit (MP Biomedicals, LLC). 6 µl of each sample contained 50 ng/µl of linearized pSTBlue, 800 µM NAD, 10 µM SirT6/truncated form, 480 µM H3, and/or 1 mM suramin as indicated. The samples sat at room temperature for 10 minutes and were loaded into 0.6% native agarose gel containing ethidium bromide. The gel was run at 100 V for 90 minutes and exposed to UV for imaging.

EXAMPLE 6

This example demonstrates the separation of SIRT6-DNA complex and determination of $K_d$ of DNA using gel electrophoresis.

25% slurry of Ni-NTA resin was incubated with 5 µM SIRT6 and 500 µM H3 peptide for 1 hour at room temperature, in addition with different concentration of pSTBlue which was linearized with BamHI or different concentration of single stranded DNA, and/or 500 µM H3 peptide. After incubation, the resin was spun at 4,000 rpm for 1 minute, and was washed with 10 fold of resin volume with 10 mM imidazole, 100 mM phosphate buffer, pH 7.5, and then 10 fold volume of resin volume with 20 mM imidazole, 10 mM phosphate buffer, pH 7.5. The SIRT6-DNA complex was separated from the resin by adding 250 mM imidazole, 100 mM phosphate buffer, pH 7.5. 10 µl of SIRT6-DNA complex was further incubated with 1 µl of 10 mM suramin (final concentration of suramin 1 mM) for 10 minutes. The DNA bound to SIRT6 was then quantified by DNA gel electrophoresis: Linearized pSTBlue was quantified by 0.8% agarose gel electrophoresis using Tris-acetate acid buffer (1×TAE) run at room temperature; single stranded DNA was quantified by 6% acrylamide gel using Tris-boric acid buffer (1×TBE) run at room temperature. The gel was stained by ethidium bromide and exposed by UV for imaging (Alpha Innotech). The control samples at each concentration of DNA but without the addition of SIRT6 were run in parallel and the amount of free DNA which did not bind to SIRT6 was quantified. After deducting the free DNA, the amount of DNA bound to SIRT6 was fitted to the Michaelis-Menten equation using the software Kaleidagraph.

In order to test if suramin competed with the binding of DNA to SIRT6, 20 ng/µl pSTBlue was incubated with 5 µM SIRT6, 25% slurry Ni-NTA resin, and/or 1 mM H3 peptide. After incubation for 1 hour at room temperature, the SIRT6-DNA-resin complex was washed with 10 and 20 mM imidazole, 100 mM phosphate buffer, pH 7.5 as described above. The SIRT6-DNA-resin complex was incubated with different concentrations of suramin. The dissociated DNA was then quantified by 0.8% agarose gel electrophoresis and the DNA level was fitted to Michaelis-Menten equation using the software Kaleidagraph.

In order to test if SIRT6 distinguished different DNA in the binding, pSTBlue was cut with different enzymes and purified by GENECLEAN™ III kit (MP Biomedicals, LLC). 20 ng/µl of pSTBlue uncut, pSTBlue cut with BamHI, or pSTBlue cut with EcoRV was incubated with 5 µM SIRT6 and/or 500 µM H3 peptide for 1 hour at room temperature. The SirT6-DNA complex was separated from the resin by 250 mM imidazole, 100 mM phosphate buffer, pH 7.5. DNA was then dissociated from SIRT6 by adding suramin to a final concentration of 1 mM and quantified by 0.8% agarose gel electrophoresis.

EXAMPLE 7

This example demonstrates the inhibition of the activation of SIRT6 by unmodified H3.

In order to test if the deacetylated H3 would inhibit the activation of SIRT6 by suramin and DNA, the enzymatic reactions were carried out in 100 mM phosphate buffer pH 7.5, 800 µM NAD, 480 µM H3, 10 µM SIRT6, 50 µM suramin or 100 ng/µl ssDNA as indicated. The unmodified H3 (no acetyl group) was added into the reaction from 0-2000 µM. AADPR was separated from other components in the reaction by a C18 reverse column (EC250/4.6 NUCLEOSIL 100-5 C18, Macherey-Nagel) using 20 mM ammonium acetate as the eluent, and then quantified by integrating their area in the chromatography at the wavelength of 260 nm. The turnover rates versus the deacetylated H3 concentration were plotted and fitted to the equation: $v=C_1-C_2/(K_i+C_3)$ using the software Kaleidagraph.

EXAMPLE 8

This example demonstrates the activation of SIRT6 by several embodiments of the invention.

Reactions containing 800 µM $NAD^+$, 500 µM H3 peptide, and 100 mM phosphate buffer at pH 7.5, with varying concentrations of nucleosides or nucleotides were initiated by addition of SIRT6 enzyme to a concentration of 11.3 µM. Reactions were incubated for 2 hours at 37° C. and quenched by addition of trifluoroacetic acid to pH 2. After centrifugation to remove precipitates, reactions were injected on HPLC for activity analysis. Production of 2'- and 3'-AADPR were analyzed at 260 nm. The results are set forth in Table 1.

TABLE 1

| Structure | Name | SIRT6 |
|---|---|---|
| (structure) | gem-diF-NR | 30% activated at 500 μM |
| (structure) | gem-diCl-NR | 30% activated at 1 mM |
| (structure) | ribo-F-NR | 17% activated at 550 μM |
| (structure) | gem-diCl-NMN | 90% activated at 500 μM |

As is apparent from the results set forth in Table 1, all of the test compounds activated SIRT6 at the indicated concentrations.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of the formula (II):

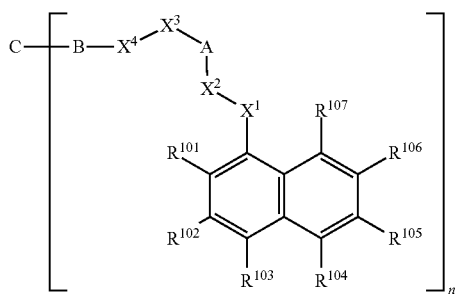

wherein each of $X^1$ and $X^3$ is —NH— and each of $X^2$ and $X^4$ is —C(=O)—,

A is selected from the group consisting of cycloalkylene, heterocycloalkylene, arylene, and heteroarylene optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, carboxyl, carbamoyl, alkoxy, sulfonate, sulfate, sulfonylamido, sulfamoyl, sulfonyl, sulfoxido, or phosphate, B is a bond, C is selected from the group consisting of —NHC(=O)NH—, —C(=O)—, alkylene, and arylene, $R^{101}$, $R^{102}$, $R^{103}$, $R^{104}$, $R^{105}$, $R^{106}$, and $R^{107}$ are independently hydrogen, alkyl, cycloalkyl, heterocycloalkyl, aryl, or heteroaryl, wherein alkyl, cycloalkyl, heterocycloalkyl, aryl, or heteroaryl are optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, carboxyl, carbamoyl, alkoxy, sulfate, sulfonylamido, sulfonyl, sulfoxido, or phosphate, and n is 2, or a pharmaceutically acceptable salt thereof.

2. The compound or salt of claim 1, wherein C is —C(=O)—.

3. The compound or salt of claim 1, wherein C is —NHC(=O)NH—.

4. The compound or salt of claim 1, wherein C is alkylene or arylene.

5. The compound or salt of claim 1, wherein A is 1,3-phenylene or 1,4-phenylene.

6. The compound or salt of claim 1, wherein $R^{103}$, $R^{105}$, and $R^{107}$ are independently sulfate or phosphate.

7. A compound selected from the group consisting of:

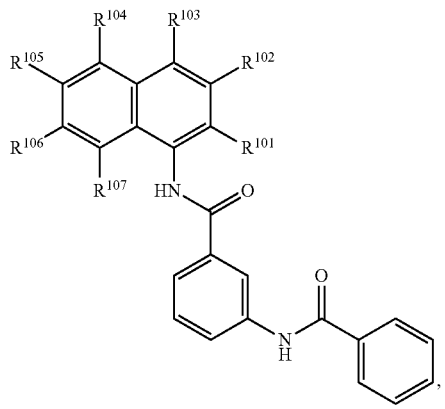

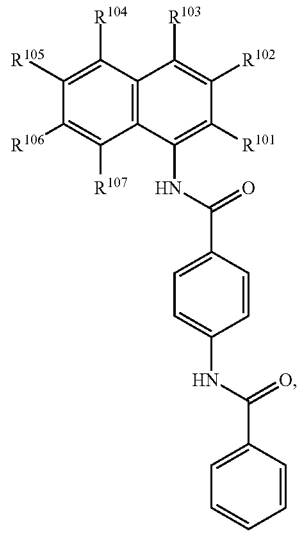

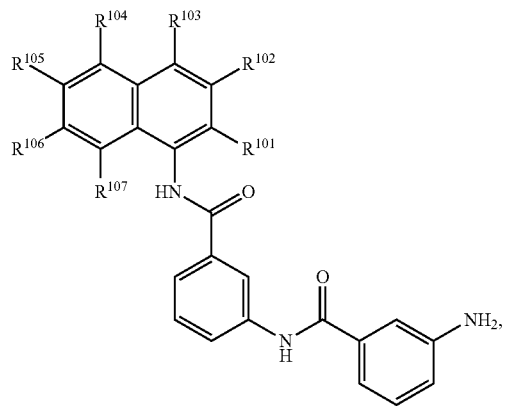
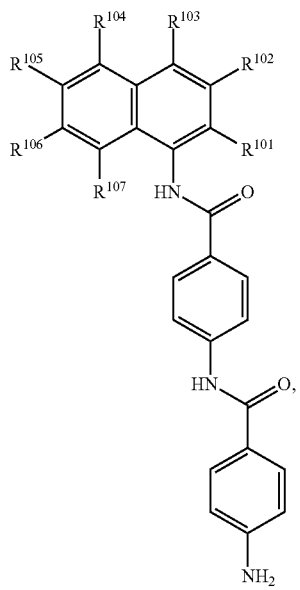
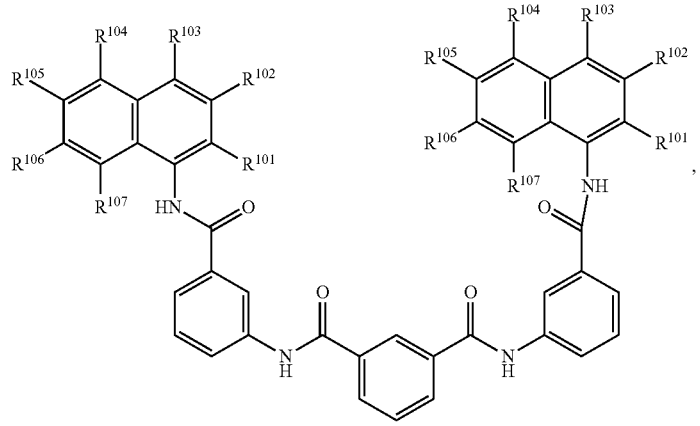
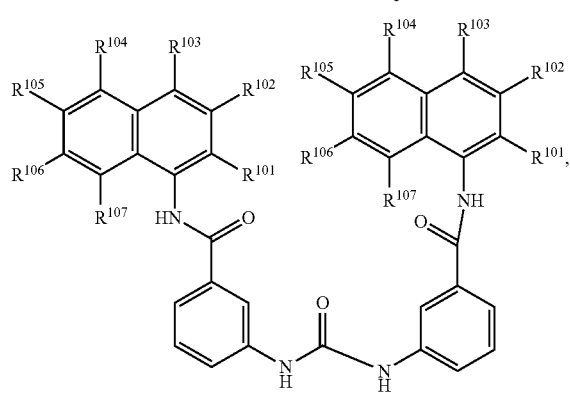
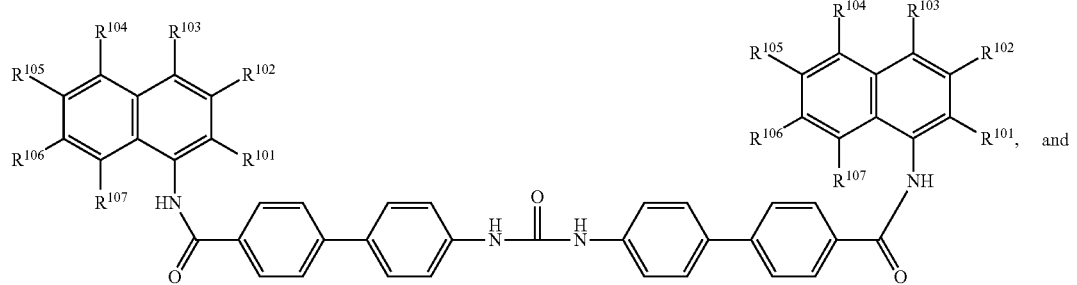

-continued

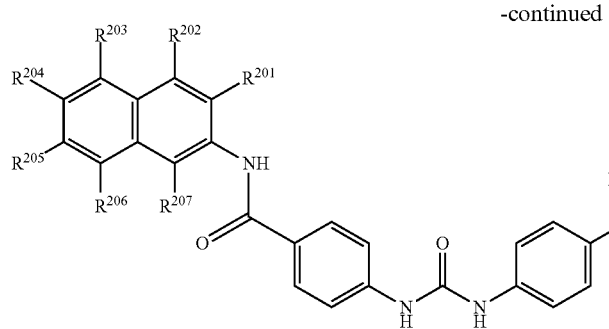
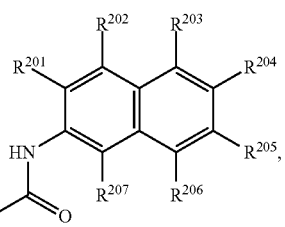

wherein $R^{101}$, $R^{102}$, $R^{103}$, $R^{104}$, $R^{105}$, $R^{106}$, $R^{107}$, $R^{201}$, $R^{202}$, $R^{203}$, $R^{204}$, $R^{205}$, $R^{206}$, and $R^{207}$ are independently hydrogen, cycloalkyl, heterocycloalkyl, aryl, or heteroaryl, wherein cycloalkyl, heterocycloalkyl, aryl, or heteroaryl are optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, carboxyl, carbamoyl, alkoxy, sulfonate, sulfate, sulfonylamido, sulfonyl, sulfoxido, or phosphate, or a pharmaceutically salt thereof.

8. A compound of the formula (III):

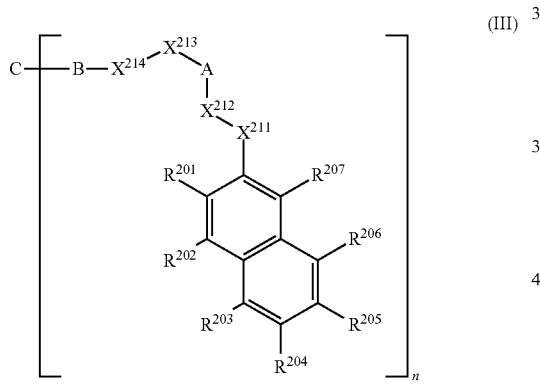

wherein each of $X^{211}$ and $X^{213}$ is —NH— and each of $X^{212}$ and $X^{214}$ is —C(=O)—, A is selected from the group consisting of cycloalkylene, heterocycloalkylene, arylene, and heteroarylene optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, carboxyl, carbamoyl, alkoxy, sulfonate, sulfate, sulfonylamido, sulfamoyl, sulfonyl, sulfoxido, or phosphate, B is a bond, C is selected from the group consisting of —NHC(=O)NH—, —C(=O)—, alkylene, and arylene, $R^{201}$, $R^{202}$, $R^{203}$, $R^{204}$, $R^{205}$, $R^{206}$, and $R^{207}$ are independently hydrogen, alkyl, cycloalkyl, heterocycloalkyl, aryl, or heteroaryl, wherein alkyl, cycloalkyl, heterocycloalkyl, aryl, or heteroaryl are optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, carboxyl, carbamoyl, alkoxy, sulfate, sulfonylamido, sulfonyl, sulfoxido, or phosphate, and n is 2, or a pharmaceutically acceptable salt thereof.

9. The compound or salt of claim 8, wherein C is —C(=O)—.

10. The compound or salt of claim 8, wherein C is —NHC(=O)NH.

11. The compound or salt of claim 8, wherein C is alkylene or arylene.

12. The compound or salt of claim 8, wherein A is 1,3-phenylene or 1,4-phenylene.

13. The compound or salt of claim 8, wherein $R^{203}$, $R^{205}$, and $R^{207}$ are independently sulfate or phosphate.

14. A compound of the formula (II):

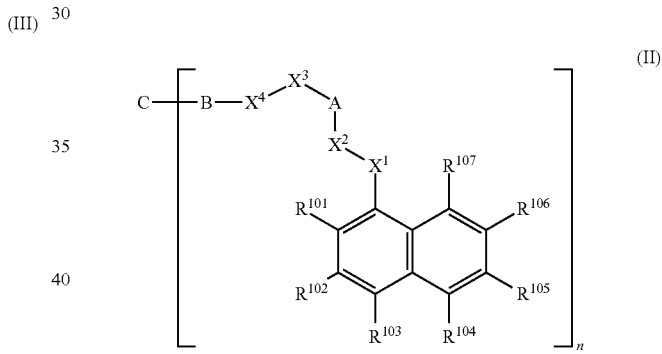

wherein $X^1$ and $X^2$ are independently selected from the group consisting of —O—, —C(=O)—, —N($R^{108}$)—, —C($R^{109}$)$_2$—, —S—, —S(=O)—, and —S(=O)$_2$— and $X^3$ and $X^4$ are absent or are independently selected from the group consisting of —O—, —C(=O)—, —N($R^{108}$)—, —C($R^{109}$)$_2$—, —C(=S)—, —S—, —S(=O)—, and —S(=O)$_2$—, A is selected from the group consisting of alkylene, cycloalkylene, heterocycloalkylene, arylene, and heteroarylene optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, carboxyl, carbamoyl, alkoxy, sulfonate, sulfate, sulfonylamido, sulfamoyl, sulfonyl, sulfoxido, or phosphate, B is a bond, C is selected from the group consisting of —NHC(=O)NH—, —C(=O)—, alkylene, and arylene, $R^{101}$, $R^{102}$, $R^{104}$, and $R^{106}$ are independently hydrogen, alkyl, cycloalkyl, heterocycloalkyl, aryl, or heteroaryl, wherein alkyl, cycloalkyl, heterocycloalkyl, aryl, or heteroaryl are optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, carboxyl, carbamoyl, alkoxy, sulfate, sulfonylamido, sulfonyl, sulfoxido, or phosphate, $R^{103}$, $R^{105}$, and $R^{107}$ are independently sulfate or phosphate, $R^{108}$ and $R^{109}$ are independently selected from the group consisting of hydrogen and $C_1$-$C_6$ alkyl, and n is 2, or a pharmaceutically acceptable salt thereof.

15. The compound or salt of claim 14, wherein C is —C(=O)—, each of $X^1$ and $X^3$ is —NH— and each of $X^2$ and $X^4$ is —C(=O)—.

16. The compound or salt of claim 14, wherein C is —NHC(=O)NH—, each of $X^1$ and $X^3$ is —NH— and each of $X^2$ and $X^4$ is —C(=O)—.

17. The compound or salt of claim 14, wherein C is alkylene or arylene, each of $X^1$ and $X^3$ or $X^{211}$ and $X^{213}$ is —NH— and each of $X^2$ and $X^4$ or $X^{212}$ and $X^{214}$ is —C(=O)—.

18. The compound or salt of claim 14, wherein A is 1,3-phenylene or 1,4-phenylene.

19. A compound of the formula (III):

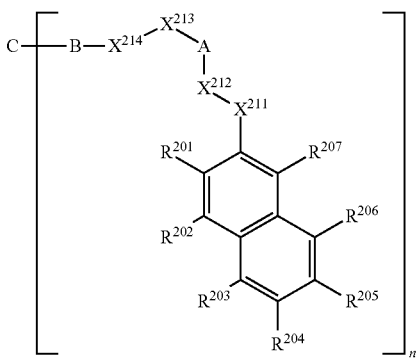

(III)

wherein $X^{211}$ and $X^{212}$ are independently selected from the group consisting of —O—, —C(=O)—, —N($R^{208}$)—, —C($R^{209}$)$_2$—, —C(=S)—, —S—, —S(=O)—, and —S(=O)$_2$— and $X^{213}$ and $X^{214}$ are absent or are independently selected from the group consisting of —O—, —C(=O)—, —N($R^{208}$)—, —C($R^{209}$)$_2$—, —C(=S)—, —S—, and —S(=O)—, and —S(=O)$_2$—, A is selected from the group consisting of alkylene, cycloalkylene, heterocycloalkylene, arylene, and heteroarylene optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, carboxyl, carbamoyl, alkoxy, sulfonate, sulfate, sulfonylamido, sulfamoyl, sulfonyl, sulfoxido, or phosphate, B is a bond, C is selected from the group consisting of —NHC(=O)NH—, —C(=O)—, alkylene, and arylene, $R^{201}$, $R^{202}$, $R^{204}$, and $R^{206}$ are independently hydrogen, alkyl, cycloalkyl, heterocycloalkyl, aryl, or heteroaryl, wherein alkyl, cycloalkyl, heterocycloalkyl, aryl, or heteroaryl are optionally substituted with alkyl, alkenyl, alkynyl, aryl, heteroaryl, arylalkyl, arylalkenyl, arylalkynyl, heteroarylalkyl, heteroarylalkenyl, heteroarylalkynyl, halo, amino, acylamido, carboxyl, carbamoyl, alkoxy, sulfate, sulfonylamido, sulfonyl, sulfoxido, or phosphate, $R^{203}$, $R^{205}$, and $R^{207}$ are independently sulfate or phosphate, $R^{208}$ and $R^{209}$ are independently selected from the group consisting of hydrogen and $C_1$-$C_6$ alkyl, and n is 2, or a pharmaceutically acceptable salt thereof.

20. The compound or salt of claim 19, wherein C is —C(=O)—, each of $X^{211}$ and $X^{213}$ is —NH— and each of $X^{212}$ and $X^{214}$ is —C(=O)—.

21. The compound or salt of claim 19, wherein C is —NHC(=O)NH—, each of $X^{211}$ and $X^{213}$ is —NH— and each of $X^{212}$ and $X^{214}$ is —C(=O)—.

22. The compound or salt of claim 19, wherein C is alkylene or arylene, each of $X^{211}$ and $X^{213}$ is —NH— and each of $X^{212}$ and $X^{214}$ is —C(=O)—.

23. The compound or salt of claim 19, wherein A is 1,3-phenylene or 1,4-phenylene.

* * * * *

SEQUENCE LISTING

```
<160> NUMBER OF SEQ ID NOS: 11

<210> SEQ ID NO 1
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is acetyllysine
<220> FEATURE:
<221> NAME/KEY: MISC_FEATURE
<222> LOCATION: (14)..(14)
<223> OTHER INFORMATION: Xaa is acetyllysine

<400> SEQUENCE: 1

Ala Arg Thr Lys Gln Thr Ala Arg Xaa Ser Thr Gly Gly Xaa Ala Pro
1               5                   10                  15

Arg Lys Gln Leu Ala Ser
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic

<400> SEQUENCE: 2

Ala Arg Thr Lys Gln Thr Ala Arg Lys Ser Thr Gly Gly Lys Ala Pro
1               5                   10                  15

Arg Lys Gln Leu Ala Ser
            20

<210> SEQ ID NO 3
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is acetyllysine
<220> FEATURE:
<221> NAME/KEY: MISC_FEATURE
<222> LOCATION: (8)..(8)
<223> OTHER INFORMATION: Xaa is acetyllysine
<220> FEATURE:
<221> NAME/KEY: MISC_FEATURE
<222> LOCATION: (12)..(12)
<223> OTHER INFORMATION: Xaa is acetyllysine
<220> FEATURE:
<221> NAME/KEY: MISC_FEATURE
<222> LOCATION: (16)..(16)
<223> OTHER INFORMATION: Xaa is acetyllysine

<400> SEQUENCE: 3

Ser Gly Arg Gly Xaa Gly Gly Xaa Gly Leu Gly Xaa Gly Gly Ala Xaa
1               5                   10                  15

Arg His Arg
```

<210> SEQ ID NO 4
<211> LENGTH: 27
<212> TYPE: DNA
<213> ORGANISM: Artificial Sequence
<220> FEATURE:
<223> OTHER INFORMATION: Synthetic

<400> SEQUENCE: 4
gctagcatgg ggctgtcgcc gtacgcg                                         27

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5
gctagcatgg cggacaaggg caagtgcggc                                      30

<210> SEQ ID NO 6
<211> LENGTH: 30
<212> TYPE: DNA
<213> ORGANISM: Artificial Sequence
<220> FEATURE:
<223> OTHER INFORMATION: Synthetic

<400> SEQUENCE: 6
gctagcatgg gcctcccgga gatcttcgac                                      30

<210> SEQ ID NO 7
<211> LENGTH: 30
<212> TYPE: DNA
<213> ORGANISM: Artificial Sequence
<220> FEATURE:
<223> OTHER INFORMATION: Synthetic

<400> SEQUENCE: 7
gctagcatga cgggtgccgg catcagcact                                      30

<210> SEQ ID NO 8
<211> LENGTH: 26
<212> TYPE: DNA
<213> ORGANISM: Artificial Sequence
<220> FEATURE:
<223> OTHER INFORMATION: Synthetic

<400> SEQUENCE: 8
ggatccccaa gcaccctggt cagctg                                          26

<210> SEQ ID NO 9
<211> LENGTH: 32
<212> TYPE: DNA
<213> ORGANISM: Artificial Sequence
<220> FEATURE:
<223> OTHER INFORMATION: Synthetic

<400> SEQUENCE: 9
ggggatccat gaagatgagc tttgcgttga ct                                   32

<210> SEQ ID NO 10
<211> LENGTH: 35
<212> TYPE: DNA
<213> ORGANISM: Artificial Sequence
<220> FEATURE:

```
<223> OTHER INFORMATION: Synthetic

<400> SEQUENCE: 10
aagcatttat cagggttatt gtctcatgag cggat                             35

<210> SEQ ID NO 11
<211> LENGTH: 35
<212> TYPE: DNA
<213> ORGANISM: Artificial Sequence
<220> FEATURE:
<223> OTHER INFORMATION: Synthetic

<400> SEQUENCE: 11
atccgctcat gagacaataa ccctgataaa tgctt                             35
```